United States Patent
Alipour et al.

(10) Patent No.: US 12,181,544 B2
(45) Date of Patent: Dec. 31, 2024

(54) RF RESONATOR ARRAY DEVICE FOR USE IN MAGNETIC RESONANCE IMAGING AND METHODS OF USE THEREOF

(71) Applicant: ICAHN SCHOOL OF MEDICINE AT MOUNT SINAI, New York, NY (US)

(72) Inventors: Akbar Alipour, New York, NY (US); Priti Balchandani, New York, NY (US); Alan C. Seifert, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

(21) Appl. No.: 17/922,912

(22) PCT Filed: May 5, 2021

(86) PCT No.: PCT/US2021/030891
§ 371 (c)(1),
(2) Date: Nov. 2, 2022

(87) PCT Pub. No.: WO2021/226237
PCT Pub. Date: Nov. 11, 2021

(65) Prior Publication Data
US 2023/0160983 A1      May 25, 2023

Related U.S. Application Data

(60) Provisional application No. 63/020,275, filed on May 5, 2020.

(51) Int. Cl.
*G01V 3/00*       (2006.01)
*A61B 5/055*    (2006.01)
(Continued)

(52) U.S. Cl.
CPC ............ *G01R 33/343* (2013.01); *A61B 5/055* (2013.01); *G01R 33/34076* (2013.01); *G01R 33/3642* (2013.01)

(58) Field of Classification Search
CPC ............ G01R 33/343; G01R 33/34076; G01R 33/3642; A61B 5/055
(Continued)

(56) References Cited

U.S. PATENT DOCUMENTS 6,850,064 B1    2/2005   Srinivasan
9,864,026 B2    1/2018   Qian et al.
(Continued)

FOREIGN PATENT DOCUMENTS

DE         4223909 A1 *  2/1994   ............ G01R 33/30
DE   102016104662 A1 *  9/2017   ......... A61B 18/1815
(Continued)

OTHER PUBLICATIONS

International Search Report and Written Opinion for corresponding Application No. PCT/US2021/030891 (mailed Aug. 18, 2021).
(Continued)

*Primary Examiner* — Walter L Lindsay, Jr.
*Assistant Examiner* — Frederick Wenderoth
(74) *Attorney, Agent, or Firm* — Troutman Pepper Hamilton Sanders LLP

(57) ABSTRACT

A radiofrequency (RF) resonator array device for use in magnetic resonance imaging (MRT), The RF resonator array device includes a substrate. An array of coupled split ring resonators are located on the substrate. Each of the coupled split ring resonators includes a first split ring resonator positioned on a first side of the substrate and a second split ring resonator positioned on a second side of the substrate located opposite the first side. The second split ring resonator is inductively coupled to the first split ring resonator.

(Continued)

Methods of making and using the RF resonator device are also disclosed.

19 Claims, 7 Drawing Sheets

(51) Int. Cl.
    *G01R 33/34*         (2006.01)
    *G01R 33/343*       (2006.01)
    *G01R 33/36*         (2006.01)

(58) Field of Classification Search
    USPC ........................................................ 324/318
    See application file for complete search history.

(56) References Cited

U.S. PATENT DOCUMENTS

| | | |
|---|---|---|
| 2003/0001573 A1 | 1/2003 | Misic |
| 2008/0042250 A1* | 2/2008 | Wilson .................... H01L 23/66 257/E25.023 |
| 2009/0216109 A1 | 8/2009 | Karmarkar et al. |
| 2010/0127707 A1 | 5/2010 | Lee et al. |
| 2013/0002253 A1 | 1/2013 | Werner et al. |
| 2015/0022284 A1* | 1/2015 | Xue .................... H01P 1/20381 333/204 |
| 2015/0076921 A1* | 3/2015 | Park ..................... H02J 50/402 307/104 |
| 2015/0241528 A1* | 8/2015 | Fackelmeier ...... G01R 33/3657 324/309 |

FOREIGN PATENT DOCUMENTS

| | | | |
|---|---|---|---|
| ES | 2344391 A1 | 8/2010 | |
| WO | 2017/157690 A1 | 9/2017 | |
| WO | WO-2018112472 A1 * | 6/2018 | ........... A61B 5/0013 |

OTHER PUBLICATIONS

Extended European Search Report for European Application No. 21800323.4 (dated Mar. 26, 2024).
Alipour et al., "An Inductively Coupled Ultra-Thin, Flexible, and Passive RF Resonator for MRI Marking and Guiding Purposes: Clinical Feasibility," Magnetic Resonance in Medicine 80:361-370 (2018).
Freire et al., "A Broadside-Split-Ring Resonator-Based Coil for MRI at 7 T." IEEE Transactions on Medical Imaging 32:1081-1084 (2013).
9.2.2 Array Coils in MISPELTER et al., "NMR Probeheads for Biophysical and Biomedical Experiments: Classroom Material." Imperial College Press (2006).
Gokyar et al., "Magnetic Resonance Imaging Assisted by Wireless Passive Implantable Fiducial e-Markers," IEEE Access 5:19693-19702 (2017).
Uğurbil et al. "Brain Imaging with Improved Acceleration and Signal-To-Noise Ratio at 7 Tesla Obtained with 64-channel Receive Array," Magnetic resonance in medicine 82:495-509 (2019).
Marqués et al., "Comparative Analysis of Edge- and Broadside-Coupled Split Ring Resonators for Metamaterial Design—Theory and Experiments," IEEE Transactions on Antennas and Propagation 51: 2572-2581 (2003).

* cited by examiner

RF RESONATOR ARRAY DEVICE FOR USE IN MAGNETIC RESONANCE IMAGING AND METHODS OF USE THEREOF

This application is a national stage application under 35 U.S.C. § 371 of PCT Application No. PCT/US2021/030891, filed May 5, 2021, which claims the benefit of Provisional Patent Application Ser. No. 63/020,275 filed May 5, 2020, which are hereby incorporated by reference in their entirety.

This invention was made with government support under grant number MH109544 awarded by the National Institutes of Health. The government has certain rights in the invention.

FIELD

The present technology relates to a radiofrequency resonator array device for use in magnetic resonance imaging and methods of use thereof.

BACKGROUND

Magnetic field strengths of magnetic resonance imaging (MRI) systems are driven continuously beyond the clinical established field strengths of 1.5 and 3 T by increasing interest in neuroscience applications, as disclosed in Ugurbil, K., "Imaging at ultrahigh magnetic fields: History, challenges, and solutions," *Neuroimage*, 168:7-32 (2018); Ugurbil, K., et al., "Ultrahigh field magnetic resonance imaging and spectroscopy," *Magn Reson Imaging*, 21(10): 1263-1281 (2003); Verma, G., et al., "Ultrahigh field MR Neuroimaging." *Top Magn Reson Imaging*, 28(3):137-144 (2019); Grisoli, M., et al., "MR imaging of cerebral cortical involvement in aceruloplasminemia," *AJNR Am J Neuroradiol*, 26:657-661 (2005); and Raichle, M. E., "Images of the mind: Studies with modern imaging techniques," *Annual Review of Psychology*, 45(1), 333-356 (1994).

Ultra-high-filed (UHF) MRI generally refers to imaging at field strengths of 7 T or more. In 2017, the "Comformite Europeene" mark was given for a 7 T MRI system indicated safety and environmental protection standards, and later the same year, the food and drug administration (FDA) approved the first clearance for clinical 7 T MRI, as disclosed in Zwaag, W., et al., "fMRI at 1.5, 3 and 7 T: characterizing BOLD signal changes," *NeuroImage*, 47:1425-1434 (2009); Beisteiner, R., et al., "Clinical fMRI: evidence for a 7 T benefit over 3 T," *Neuroimage*, 57(3): 1015-1021 (2011); and Vu, A. T., et al., "High resolution whole brain diffusion imaging at 7 T for the Human Connectome Project," *Neuroimage*, 122:318-331 (2015); Wu, X., et al., "A generalized slab-wise framework for parallel transmit multiband RF pulse design," *Magn Reson Med*, 75(4):1444-1456 (2016).

Currently, imaging above 8 T is available only on research protocols approved by an institutional review board and the informed consent of the subjects, as disclosed in Sadeghi-Tarakameh, A., et al., "In vivo human head MRI at 10.5 T: A radiofrequency safety study and preliminary imaging results," *Magn Reson Med*, 84(1):484-496 (2020); and Norris, D. G., et al., "High field human imaging," *J Magn Reson Imaging*, 19(4):513 (2004). 7 T and higher UHF magnets provide opportunities to satisfy the high demand of increased signal-to-noise ratio (SNR), detailed spatial information, and functional contrast, as disclosed in Marques, J. P., et al., "On the origin of the MR image phase contrast: an in vivo MR microscopy study of the rat brain at 14.1 T," *Neuroimage*, 46(2):345-352 (2009); and Marques, J. P., et al., "Cerebellar cortical layers: in vivo visualization with structural high-field-strength MR imaging," *Radiology*, 254 (3):942-948 (2010). With the available higher SNR at 7 T, various studies performed high-resolution MRI imaging of the brain including skull base and cerebellum revealing cerebellar cortical layers. It is well known that MRI at 7 T can provide much better signal sensitivity compared with lower field strengths. This can be used to reduce the scan time, while improving the spatial resolution required for visualizing small sized deep features in the brain.

However, many UHF MRI experiments are designed for only describing individual sub-regions of the brain in more detail without covering the whole-brain, specifically the central nervous system (i.e., the cerebrum, cerebellum, brainstem, and spinal cord). The variety of commercially available 7 T radiofrequency (RF) coils are still limited, due to the technical challenges associated with wavelength effect (high operating frequency), such as inhomogeneity of the transmitted magnetic field into the subject and asymmetric transmit and receive RF field patterns for surface coils, as disclosed in Adriany, G., et al., "A half-volume coil for efficient proton decoupling in humans at 4 tesla," *J Magn Reson*, 125(1):178-184 (1997); Van de Moortele, P. F., et al., "B(1) destructive interferences and spatial phase patterns at 7 T with a head transceiver array coil," *Magn Reson Med*, 54(6):1503-1518 (2005); Van de Moortele, P. F., et al., "B(1) destructive interferences and spatial phase patterns at 7 T with a head transceiver array coil," *Magn Reson Med*, 54(6):1503-1518 (2005); Pfaffenrot, V., et al., "An 8/15-channel Tx/Rx head neck RF coil combination with region-specific $B_1^+$ shimming for whole-brain MRI focused on the cerebellum at 7 T," *Magn Reson Med*, 80(3):1252-1265 (2018); Keltner, J. R., et al., "Electromagnetic fields of surface coil in vivo NMR at high frequencies," *Magn Reson Med*, 22(2):467-480 (1991); Vaughan, J. T., et al., "7 T vs. 4 T: RF power, homogeneity, and signal-to-noise comparison in head images," *Magn Reson Med*, 46(1):24-30 (2001); and Foo, T. K., et al., "Reduction of RF penetration effects in high field imaging," *Magn Reson Med*, 23(2):287-301 (1992).

Most commercial head coils designed for brain imaging at 7 T today are used for imaging the specific region (e.g. the cerebrum) with a steep gradient in signal often observed in the lower brain and other inferior areas of the head, as disclosed in Yang, Q. X., et al., "Manipulation of image intensity distribution at 7.0 T: passive RF shimming and focusing with dielectric materials," *J Magn Reson Imaging*, 24(1):197-202 (2006); Sreenivas, M., et al., "A simple solution for reducing artefacts due to conductive and dielectric effects in clinical magnetic resonance imaging at 3 T," *Eur J Radiol*, 62(1):143-146 (2007). The most commonly commercially available used 7 T head coil is Nova 1Tx32Rx coil (1 Transmit/32 Receive, Nova Medical, Wilmington, MA), which consists of a relatively short single channel birdcage volume transmit coil surrounding a 32 channel receive array. This coil is designed principally for brain imaging with a limited FOV relative to commercial head coils used at lower field strengths, where the RF excitation is mostly transmitted with the system's large whole body birdcage coil, as disclosed in Wu, X., et al., "A generalized slab-wise framework for parallel transmit multiband RF pulse design," *Magn Reson Med*, 75(4):1444-1456 (2016). Its physical location in the posterior cranial fossa and anatomical diversity, combined with its small size, makes the cerebellum a challenging area of interest for UHF MRI.

In particular, it is possible to handle the $B_1^+$ non-uniformity caused by the RF wavelength effect using active and passive RF shimming techniques. Parallel transmission (pTx) is an active RF shimming technique that significantly improved $B_1^+$ homogeneity in the human brain at UHF MRI systems, as disclosed in Adriany, G., et al., "A half-volume coil for efficient proton decoupling in humans at 4 tesla," *J Magn Reson*, 125(1):178-184 (1997); Van de Moortele, P. F., et al., "B(1) destructive interferences and spatial phase patterns at 7 T with a head transceiver array coil," *Magn Reson Med*, 54(6):1503-1518 (2005); and Van de Moortele, P. F., et al., "B(1) destructive interferences and spatial phase patterns at 7 T with a head transceiver array coil," *Magn Reson Med*, 54(6):1503-1518 (2005). To achieve whole-brain MRI, a generalized pTx design structure was introduced and signified its utility for covering whole-brain at 7 T. Specifically, they demonstrated the utility of pTx in the cerebellum in the context of a 7 T whole-brain acquisition. The results indicated that pTx can significantly enhance $B_1^+$ uniformity across the entire brain compared with a single-transmit configuration (i.e., Nova 1Tx32Rx coil). However, pTx systems reported high specific-absorption-rate (SAR) compared with a single-transmit configuration, as disclosed in Wu, X., et al., "A generalized slab-wise framework for parallel transmit multiband RF pulse design," *Magn Reson Med*, 75(4):1444-1456 (2016).

The use of dielectric pads (DPs), i.e., high permittivity material with $\varepsilon_r>50$, as a passive RF shimming method in MRI has been proposed to reduce inhomogeneity, improve SNR, and increase transmit efficiency, as disclosed in Van Gemert, J., et al., "An Efficient Methodology for the Analysis of Dielectric Shimming Materials in Magnetic Resonance Imaging," *Trans Med Imaging*, 36(2):666-673 (2017); Haines, K., et al., "New high dielectric constant materials for tailoring the $B_1^+$ distribution at high magnetic fields," *J Magn Reson*, 203(2):323-327 (2010); Teeuwisse, W. M., et al., "Simulations of high permittivity materials for 7 T neuroimaging and evaluation of a new barium titanate based dielectric," *Magn Reson Med*, 67(4):912-918 (2012); Snaar J. E., et al., "Improvements in high-field localized MRS of the medial temporal lobe in humans using new deformable high-dielectric materials," *NMR Biomed*, 24(7):873-879 (2011); Teeuwisse, W. M., et al., "Quantitative assessment of the effects of high-permittivity pads in 7 Tesla MRI of the brain," *Magn Reson Med*, 67(5):1285-1293 (2012); Vaidya, M. V., et al., "Improved detection of fMRI activation in the cerebellum at 7 T with dielectric pads extending the imaging region of a commercial head coil," *J Magn Reson Imaging*, 48(2):431-440 (2018); O'Brien, K. R., et al., "Dielectric pads and low-B1+ adiabatic pulses: complementary techniques to optimize structural T1 w whole-brain MP2RAGE scans at 7 tesla," *J Magn Reson Imaging*, 40(4):804-812 (2014); and O'Reilly, T. P. A., et al., "Practical improvements in the design of high permittivity pads for dielectric shimming in neuroimaging at 7 T," *J Magn Reson*, 270:108-114 (2016). These significant benefits can be explained by the modified Ampere's law; attribution of displacement currents within the DPs that add to the local magnetic field.

Recently, high permittivity ($\varepsilon_r>100$) composite materials constructed from calcium or barium titanate powders mixed with deuterium oxide for greater advantages in MRI applications have been employed as disclosed in Snaar J. E., et al., "Improvements in high-field localized MRS of the medial temporal lobe in humans using new deformable high-dielectric materials," *NMR Biomed*, 24(7):873-879 (2011). A variety of MRI experiments have been performed using DPs in association with a commercial head coil at 7 T. The DPs positioning on one or both sides of the head can improve SNR and signal homogeneity in the cerebrum.

Although the using DPs in conjunction with the head coil displayed improved excitation, SNR, and coverage in the anterior portion of the cerebellum, it also resulted in a strong RF field gradient across the cerebellum in the anterior-posterior direction. This consequently resulted in both lower SNR and lower excitation in the posterior cerebellum when the DPs were applied, as disclosed in O'Reilly, T. P. A., et al., "Practical improvements in the design of high permittivity pads for dielectric shimming in neuroimaging at 7 T," *J Magn Reson*, 270:108-114 (2016). Another limitation was the large thickness (z 2 cm) of DPs, which occupied considerable amount of the area inside the head coil.

Developing new RF pulses is another approach to overcome the $B_1^+$ inhomogeneity problem in UHF MRI. A matched-phase adiabatic RF pulse pair was developed using the Shinnar Le-Roux algorithm in spin echo (SE) sequences to provide immunity to the inhomogeneous $B_1^+$ field at 7 T, as disclosed in Balchandani, P., et al., "Self-refocused adiabatic pulse for spin echo imaging at 7 T," *Magn Reson Med*, 67(4):1077-1085 (2012). The pulse pair was modified into a single self-refocused pulse to minimize the echo time. The self-refocused adiabatic pulses produced $B_1^+$ distribution that was substantially more uniform than those achieved using a standard SE sequence. This method is limited to SE sequences and may result in a high-energy abortion rate.

A method based on universal pulses was also presented to minimize the $B_1^+$ inhomogeneity in brain imaging at 7 T, as disclosed in Gras, V., et al., "Design of universal parallel-transmit refocusing k T-point pulses and application to 3D $T_2$-weighted imaging at 7 T," *Magn Reson Med*, 80(1):53-65 (2018). This technique avoids systematic measurement of the RF and static field profiles for each subject, which are required in most pulse design protocols. Such pulses do not include the subject-specific field distributions, but yet are aimed to significantly improve performance compared with the conventional RF shim modes.

The present technology is directed to overcoming these and other deficiencies in the art.

SUMMARY

One aspect of the present technology relates to a radiofrequency (RF) resonator array device for use in magnetic resonance imaging (MRI). The RF resonator array device includes a substrate. An array of coupled split ring resonators are located on the substrate. Each of the coupled split ring resonators includes a first split ring resonator positioned on a first side of the substrate and a second split ring resonator positioned on a second side of the substrate located opposite the first side. The second split ring resonator is inductively coupled to the first split ring resonator.

Another aspect of the present technology relates to a method of making a radiofrequency (RF) resonator array device for use in magnetic resonance imaging (MRI). The method includes providing a substrate. An array of coupled split ring resonators are located on the substrate. Each of the coupled split ring resonators includes a first split ring resonator positioned on a first side of the substrate and a second split ring resonator positioned on a second side of the substrate located opposite the first side. The second split ring resonator is coupled to the first split ring resonator.

A further aspect of the present technology relates to a method A method of generating a magnetic resonance image (MRI) using an MRI device. The method includes providing a radiofrequency (RF) resonator array device. The RF resonator device includes a substrate and an array of coupled split ring resonators located on the substrate. Each of the coupled split ring resonators includes a first split ring resonator positioned on a first side of the substrate and a second split ring resonator positioned on a second side of the substrate located opposite the first side. The second split ring resonator is coupled to the first split ring resonator and is positioned in an orientation rotated 180 degrees with respect to the first split ring resonator. The RF resonator array device is positioned near a portion of a patient's anatomy to be imaged using the MRI device. An MRI image of the portion of the patient's anatomy is obtained using the MRI device. The RF resonator array device inductively couples to a radiofrequency coil of the MRI device during radiofrequency transmission and reception to provide additional flux and amplify the receive MR signal during operation of the MRI device.

The present technology provides an inductively coupled radiofrequency (RF) resonator array device that may be employed to improve brain magnetic resonance imaging. The RF resonator array device may be utilized in a passive RF shimming technique to improve brain MRI focusing of the cerebellum, for example, extending the sensitivity of a commercial head coil at 7 T, for example. The passive RF resonator array device of the present technology advantageously improves the transmit efficiency of the head coil and enhance the signal sensitivity at 7 T brain MRI, for example.

The present technology also advantageously provides an efficient method to improve brain MRI focusing on the cerebellum at 7 T, for example, using a wireless passive RF array device to extend the anatomical coverage of a standard commercial head coil. The array includes critically overlapped coupled-split-ring resonators. The method provides RF performance and safety with average and local specific absorption rate (SAR) measurements that do not exceed current recommended limits. The method provides an increase in transmit efficiency and signal-to-noise ratio (SNR), particularly in the cerebellum, temporal lobes, and inferior regions of the CNS in a brain MRI. This method could advantageously increase the feasibility of commercial head coils at 7 T for whole brain MRI, functional MRI, and other MRI applications.

DETAILED DESCRIPTION

One aspect of the present technology relates to a radiofrequency (RF) resonator array device for use in magnetic resonance imaging (MRI). The RF resonator array device includes a substrate. An array of coupled split ring resonators are located on the substrate. Each of the coupled split ring resonators includes a first split ring resonator positioned on a first side of the substrate and a second split ring resonator positioned on a second side of the substrate located opposite the first side. The second split ring resonator is coupled to the first split ring resonator.

Figure 1:
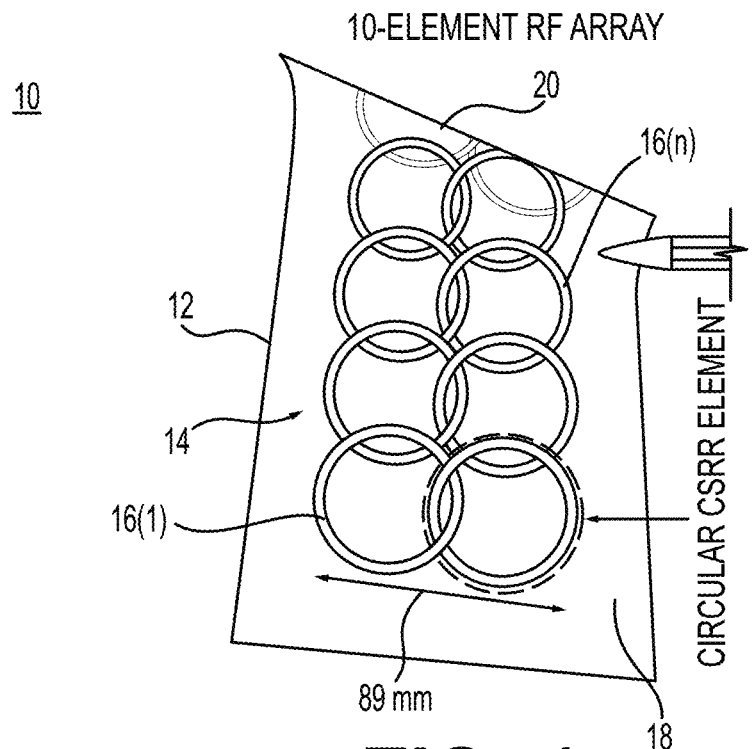
FIG. 1 is an illustration of an exemplary radiofrequency (RF) resonator array device of the present technology.

Exemplary RF resonator array device 10 is illustrated in FIG. 1. RF resonator array device 10 includes substrate 12 and an array of coupled split ring resonators (CSSRs) 14 including CSSRs 16(1)-16(n) located on substrate 12, although the RF resonator array device may include additional elements or components in other combinations. RF resonator array device 10 provides a wireless, passive device. RF resonator array device 10 may be employed in magnetic resonance imaging to improve brain MRI focusing of the cerebellum, for example, although RF resonator array device 10 may be employed for other uses. RF resonator array device 10 can be employed using a standard commercial MRI head coil, for example, to extend the sensitivity of the commercial head coil at 7 T and above as described herein. RF resonator array device 10 includes no lumped element components, which avoids possible safety concerns (such as heating), during use with an MRI device.

Figure 2:
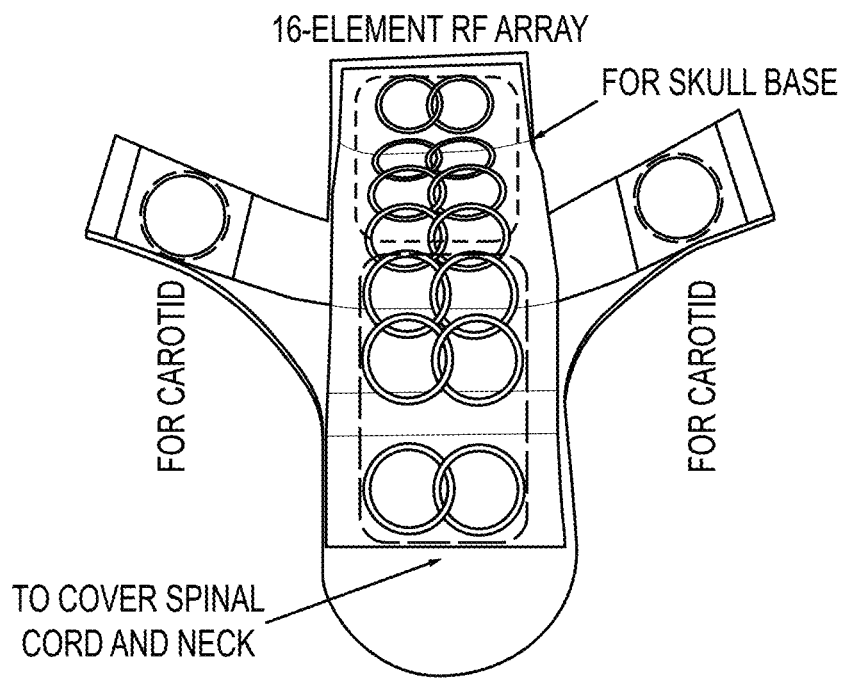
FIG. 2 illustrates another exemplary RF resonator array device of the present technology.

Substrate 12 includes first side 18 and second side 20 located opposite of first side 18. Substrate 12 can have various geometries based on the application and the anatomy to be imaged. In one example, substrate 12 is formed as shown in FIG. 2 in order to image a patient's brain stem. In particular, substrate 12 in FIG. 2 is configured to have a geometry to make it conform to the back of the neck, sides of the neck, back of the lower head, and upper back of the patient. In one example, substrate 12 is formed of a flexible dielectric material, such as Kapton or Peek. The use of a flexible material allows substrate 12 to conform to the patient's anatomy during use. Substrate 12 has a thickness between about 50 micrometers and about 500 micrometers. In one example, substrate 12 has a thickness of about 200 micrometers. The size of substrate 12 depends on the operating frequency of the MRI machine and imaging area. Substrate 12 may range from about 2 cm to about 20 cm (in diameter or in diagonal), by way of example.

Array of CSSRs 14 is located on substrate 12 and includes CSSRs 16(1)-16(n). Referring now to more specifically to FIGS. 5A-5D, an exemplary CSSR 16(1) is illustrated (without substrate 12) in FIG. 5A selected from the RF resonator array in FIG. 5C. Although CSSR 16(1) is described with reference to FIG. 5A, it is be understood that each of the additional CSSRs are the same in structure and operation as CSSR 16(1). Further, CSSR 16(1) may have other configurations, such as shown in FIGS. 3a and 3c, as described in further detail below.

Figure 3A:
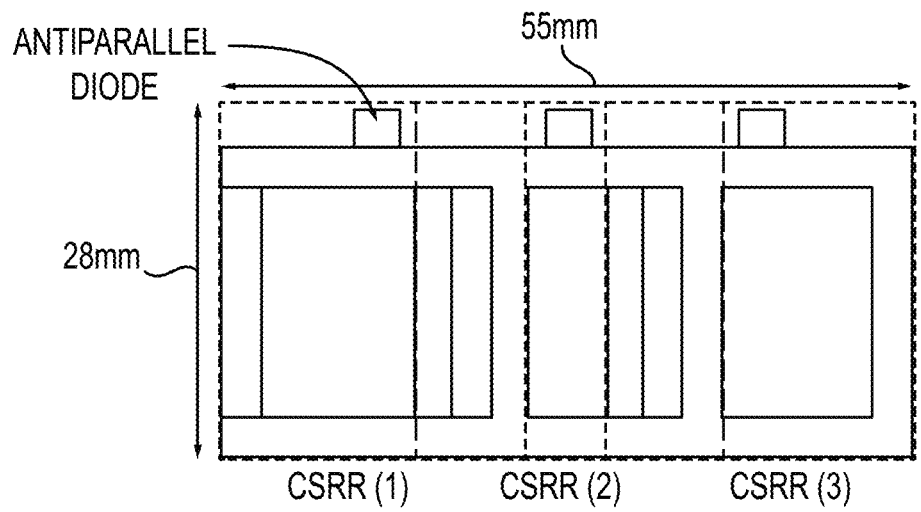
FIGS. 3A-3C illustrate schematics of another exemplary CSSR of the present technology.
Figure 3B:
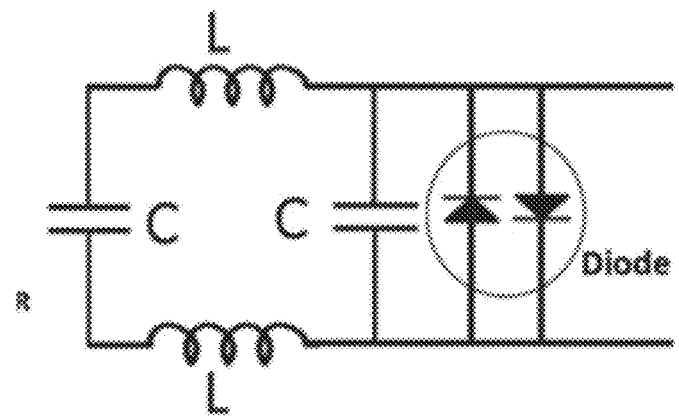
Figure 3C:
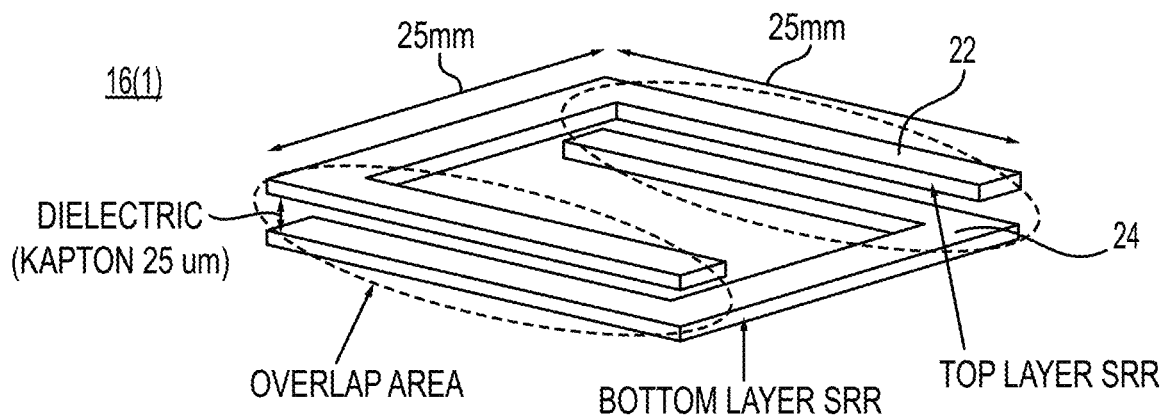
Figure 5:
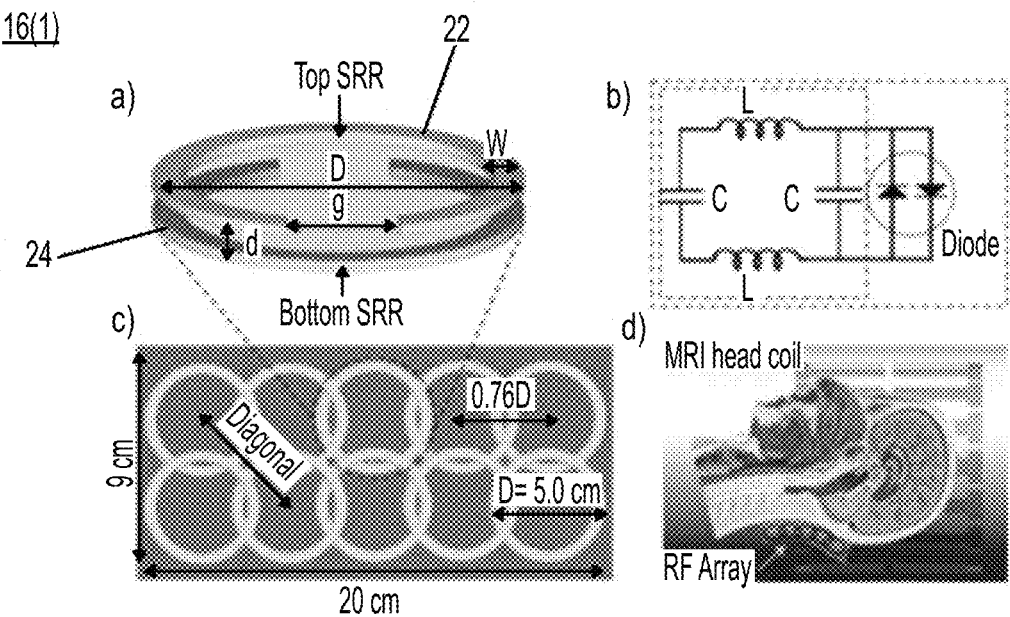
FIG. 5A illustrates 3D schematic of a coupled-split-ring resonator (CSRR), which includes two anti-oriented SRRs. A dielectric substrate is sandwiched between two layers of SRR. CSRR design parameters also are shown in 3D model, D is the average diameter, W is the metallization width, d is the dielectric thickness, and g is the gap width.
FIG. 5B illustrates an electrical circuit model of the CSRR. C is the built in distributed capacitance value and L is the inductance. An anti-parallel cross diode is used to decouple the CSRR from RF excitation (diode is not shown in the 3D model).
FIG. 5C illustrates a schematic of a 10-element wireless passive RF resonator array including the CSSR shown in FIG. 5A.
FIG. 5D illustrates an exemplary RF resonator array device in use with a standard MRI coil.

Referring now to FIGS. 3A, 3C, and 5A, CSSR 16(1) is formed as a layered structure such that CSSR 16(1) includes first split ring resonator 22 positioned on first side 18 of substrate and second split ring resonator 24 positioned on 20 second side of substrate 12 and coupled to first split ring resonator 22. First split ring resonator 22 and second split ring resonator 24 are formed of a conductive material. In an axial view (i.e., top or bottom), CSSR 16(1) appears to form a continuous loop of conductive material, but an orthogonal view shows that first split ring resonator 22 and second split ring resonator 24 are overlapping conductive structures that are not in isolation a continuous loop. The overlapping conductive structures are separated by substrate 12, which is formed of a dielectric material. Although two overlapping conductive structures, i.e., first split ring resonator 22 and second split ring resonator 24 are shown in FIGS. 3a, 3c, and 5A, there could be more than two overlapping conductive structures. Referring more specifically to FIG. 5A, while two overlapping structures create, in an axial view, a continuous loop of greater than 360 degrees but less than 720 degrees, any overlapping loops of greater than 360 degrees are contemplated. Second split ring resonator 24 is positioned in an orientation rotated 180 degrees with respect to first split ring resonator 22. The critical overlapping between neighboring CSSRs serves to reduce the inductive coupling between CSSRs. The overlap is based on the critical loop center-to-center distance to minimize mutual inductance.

Referring again to FIG. 1, each of CSSRs 16(1)-16(n) in the array of CSSRs 14 are configured to inductively couple to a magnetic coil of an MRI device. Array of CSSRs 14 is configured to provide additional flux during a transmit phase of the MRI device and to improve receive MR signal during a receive phase of the MRI device during operation of the MRI device. Each of CSSRs 16(1)-16(n) is tuned to a resonance frequency that is equal to the Larmor frequency of the MRI device based on a field strength of the MRI device. In one example, the resonance frequency is about 297 MHz based on a 7 T MRI device, although other resonance frequencies may be employed based on the MRI device being utilized. Each of CSSRs 16(1)-16(n) are configured to generate a local magnetic field that increases resonator signal intensity near CSSRs 16(1)-16(n) during operation of the MRI device.

In one example, one or more of CSSRs 16(1)-16(n) includes overlap location 26 on substrate 12 that overlaps with another one of CSSRs 16(1)-16(n). Overlap location 26 is based on a critical loop center-to-center distance value between the overlapping CSSRs in order to reduce induction during operation. In one example, the center-to-center distance is about 31.5 millimeters, although other center-to-center distances may be employed.

In this example, 10 CSSRs are employed in a 2×5 array although other numbers of CSSRs in other configurations may be employed. For example, FIG. 2 illustrates a 16 CSSR element array. The array in FIG. 2 includes CSSRs configured on substrate 12 in a geometrical configuration such that the CSSRs can be located near the patient's skull base, spinal cord and neck, and carotid, for example. The array in FIG. 2 further includes CSSRs that do not include an overlap location. FIGS. 3a and 3c illustrate another exemplary device with three CSSRs. It is to be understood that any number of CSSRs may be employed in various configurations based on the anatomy to be imaged. The number of CSSRs depends on the operating frequency of the MRI machine device and the imaging area.

Referring again to FIG. 1, in this example CSSRs 16(1) and 16(2) are circular in shape, although CSSRs may have other configurations. For example, CSSRs with 90 degree corners to have a rectangular or square shape as shown in FIGS. 3a and 3b may be employed. However, CSSRs 16(1)-16(n) may have other configurations including only curved sections (e.g., circle, oval, or a combination), 90 degree corners (e.g., square or rectangle), or other angles other than 90 degrees to form a polygon (e.g., pentagon, hexagon, and octagon). In other examples, CSSRs 16(1)-16(n) may include curved sections combined with straight sections and angles to form custom shapes.

Another aspect of the present technology relates to a method of making a radiofrequency (RF) resonator array device for use in magnetic resonance imaging (MRI). The method includes providing a substrate. An array of coupled split ring resonators are located on the substrate. Each of the coupled split ring resonators includes a first split ring resonator positioned on a first side of the substrate and a second split ring resonator positioned on a second side of the substrate located opposite the first side. The second split ring resonator is coupled to the first split ring resonator.

A further aspect of the present technology relates to a method A method of generating a magnetic resonance image (MRI) using an MRI device. The method includes providing a radiofrequency (RF) resonator array device. The RF resonator device includes a substrate and an array of coupled split ring resonators located on the substrate. Each of the coupled split ring resonators includes a first split ring resonator positioned on a first side of the substrate and a second split ring resonator positioned on a second side of the substrate located opposite the first side. The second split ring resonator is coupled to the first split ring resonator and is positioned in an orientation rotated 180 degrees with respect to the first split ring resonator. The RF resonator array device is positioned near a portion of a patient's anatomy to be imaged using the MRI device. An MRI image of the portion of the patient's anatomy is obtained using the MRI device. The RF resonator array device inductively couples to a magnetic coil of the MRI device during the obtaining to provide additional flux and amplify the receive MR signal during operation of the MRI device.

In one example, RF resonator array device 10 is used to obtain an MRI image of the patient's brain, although RF resonator device 10 may be utilized to perform MRI on other portions the patient's anatomy. In one example, the MRI image is obtained at a field strength of at least 7 T, although other field strengths may be employed when using RF resonator array device in conjunction with an MRI device. During operation, each of CSSRs 16(1)-16(n) in RF resonator array device 10 inductively couple to a magnetic coil of the associated MRI device to provide additional flux during a transmit phase of the MRI device, and to improve receive MR signal during a receive phase of the MRI device. CSSRs 16(1)-16(n) generate a local magnetic field that increases resonator signal intensity near each of CSSRs 16(1)-16(n) during operation of the MRI device.

EXAMPLES

The present description is further illustrated by the following examples, which should not be construed as limiting in any way.

Example 1—RF Resonator Array

An effective approach to improve transmit efficiency and signal enhancement in 7 T MRI systems was designed and validated. A wireless passive RF resonator array providing solution for $B_1^+$ inhomogeneity problem was constructed and tested. The array (9×20 cm$^2$) included 10 elements aligned in a form of 2×5 matrix. Each element was a CSRR (circular, D=47 mm), where the elements were decoupled from each other using the critical overlap technique and were tuned to operate at the Larmor frequency of a 7 T MRI scanner (297 MHz). CSRR design parameters were optimized using EM simulation (CST) and then applied for array modeling. To prevent $B_1^+$ over-flipping strongly coupled elements were decoupled from RF excitation using anti parallel diode. A flexible thin film (200 μm) substrate was used in the array fabrication, which was sandwiched between two metal layers. Flexible architecture of the array increases its implementation in the various positions.

A wireless passive RF array device was used in conjunction with a standard head coil to improve the whole-brain MRI at 7 T by improving the receive signal sensitivity and transmit efficiency in the brain, particularly in the cerebellum. The transmit and receive inductive coupling of the RF array with the RF excitation and magnetization vector, respectively, not only improve the FA and receive sensitivity near the brainstem and cerebellum, but also extend the anatomical coverage to visualize regions inherently far from the coil. A commercial head coil was used to demonstrate the improvement in coil sensitivity. The coil suffered from limited sensitivity at the temporal lobes and cerebellum, which was improved by placing the RF array near inferior regions of the head.

The array performance was evaluated using EM simulations, bench tests, and MRI experiments. It was demonstrated, in both simulations and experiments, that the sensitivity and the transmit efficiency of a commercial head coil at 7 T can be improved in the skull base and cerebellum using a passive RF array. This enhancement in SNR was used for improving whole brain imaging including the cerebellum, where the standard coil is limited due to poor transmit and receive sensitivity.

SAR distribution of the standard coil was manipulated in the presence of the RF array. The maximum 10 gr averaged and local SAR decreased with array in the center, but increased at the periphery of the coil, while producing greater transmit efficiency at the periphery (up to ~ 2.5 cm) and almost the same at the center. Transmit inductive coupling between the RF excitation and some of elements in the array could be considered as a major reason of SAR amplification. Temperature tests also reported a maximum local SAR gain of about 33% in the presence of the array. Although the simulated and measured local and average SAR values increased with addition of the RF array, they were below limits recommended by the FDA and IEC.

The results showed that in addition to a higher SNR in the cerebellum in the presence of the array, higher SNR was observed in the other regions of the brain. FA maps and SNR calculations results were consistent with the obtained GRE, MP-RAGE, and TSE MR images, which showed improved visibility of the brainstem and cerebellum. These images also showed improved signal and contrast in the central and frontal regions of the brain. The experimental SNR analysis scaled by the $B_1^+$ determined that the achieved enhancement in SNR of 2- to 4-fold was mainly due to the improved transmit efficiency and partially due to received-only coupled sensitivity improvement. The CNR analysis of the images obtained with/without the proposed array also showed that the contrast was improved in the presence of the array.

Although this device focuses on brain MRI at 7 T, it can be modified to operate at different field strengths for various regions of interest imaging.

Example 2—Materials and Methods

A wireless passive radiofrequency (RF) resonator array was developed that was aimed to improve the transmit efficiency and signal sensitivity in a conventional head coil at 7 T MRI. To realize this, the array was placed against the posterior and inferior portion of the head inside the head coil to improve whole-brain MRI focusing on the cerebellum.

The design parameters and electrical characteristics of a single RF resonator were investigated, and then applied the optimized parameters to array modeling. A single passive radiofrequency (RF) resonator was electromagnetically simulated by varying key design parameters. An array that included 10 RF resonators was constructed based on the optimized design. The array was designed to provide: (a) improved transmit efficiency, and (b) enhanced receive signal sensitivity. In particular, a 10-element inductively-coupled RF resonator array was designed for placement inside a commercial head coil to enhance the transmit field homogeneity and to improve the receive signal sensitivity. Each element is a coupled-split-ring resonator (CSRR), which are decoupled for each other using a critical overlap technique. Electromagnetic (EM) simulations were used to optimize the design parameters for the CSRRs and to determine the array configuration. The electrical characteristics of the CSRRs and decoupling level were evaluated using a vector network analyzer. EM simulations and thermal tests were also performed to evaluate RF safety.

EM simulations and experimental methods were utilized to investigate the technical potential of the array in transmit efficiency and signal sensitivity without increasing the SAR. Phantom and ex-vivo MRI experiments were performed to assess transmit efficiency and signal sensitivity in the presence of the array. The simulation and experimental data were compared for with/without the array to assess the array performance. Network analyzer tests were performed to measure electrical characteristics (Q-factor, resonance frequency, and decoupling values) of the device. SNR, $B_1^+$ map, and RF safety studies were performed using a conventional head coil with and without the passive RF resonator array. Finally, the device imaging performance was evaluated using a cadaver brain at 7 T MRI. The MR imaging, contrast-to-noise ratio (CNR), and SNR analysis were performed using the cadaver brain in a 7 T MRI system.

Example 3—Theoretical Background

Figure 4:
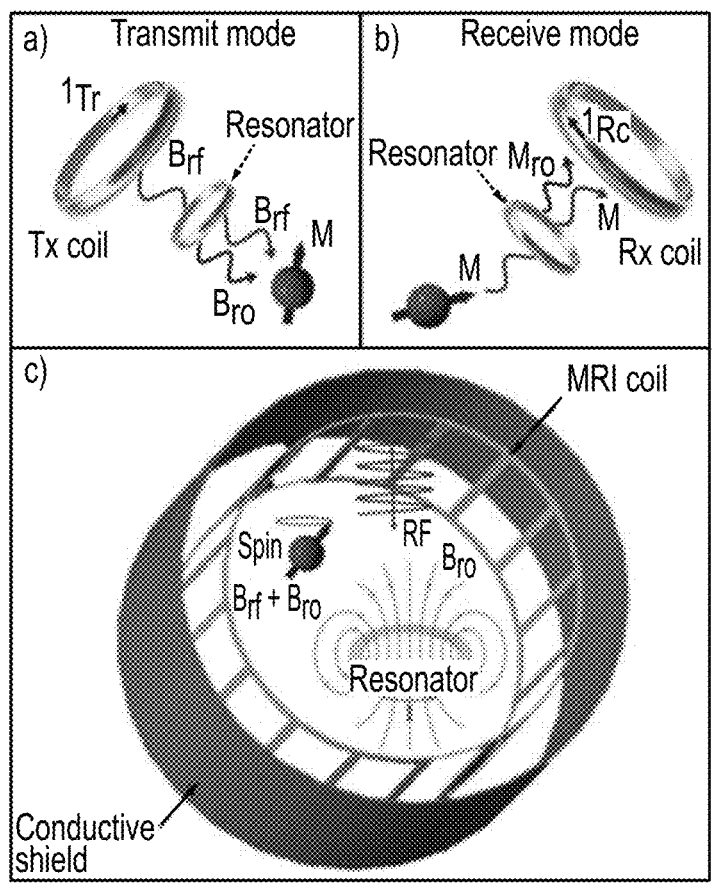
FIG. 4A illustrates passive RF resonator behavior during RF excitation, the resonator locally amplifies transmit field generated by transmit (Tx) coil and resulted in larger transverse magnetization.
FIG. 4B illustrates passive RF resonator behavior during the receive phase. The magnetization vector (M), induces current (IRc) on receive (Rx) coil, resonator coupling with M and Rx coil results in induced signal amplification.
FIG. 4C illustrates the circularly-polarized transmit magnetic field of the transmit coil inductively coupled to the resonator, the reaction of the resonator with excitation field leads to circulating current in the resonator, which results in a secondary magnetic field in the resonator vicinity.

Inductive coupling between the passive radiofrequency (RF) resonator tuned to the Larmor frequency and MRI coils results in local $B_1^+$ and MR signal enhancement, as disclosed in Duan, G., et al., "Boosting magnetic resonance imaging signal-to-noise ratio using magnetic metamaterials," *Commun Phys*, 2(1):35 (2019); Zhang, X., "Sensitivity enhancement of traveling wave MRI using free local resonators: an experimental demonstration," *Quant Imaging Med Surg*, 7(2):170-176 (2017); and Gokyar, S., et al., "Wireless deep-subwavelength metamaterial enabling sub-mm resolution magnetic resonance imaging," *Sensors and Actuators A: Physical*, 274:211-219 (2018), the disclosures of which are incorporated by reference herein in their entirety. This principle originates from; (a) inductive coupling between the resonator and RF excitation which leads to effective flip angle (FA) increasing, as shown in FIG. 4A, and (b) inductive coupling between the resonator and magnetization vector (M) during the reception which leads to receive-signal amplification as shown in FIG. 4B. The transmit magnetic flux $\Phi_{rf}$ of the transmit coil inductively couples to the RF resonator, the reaction of the resonator with transmit flux leads to circulating current in the resonator, which results in a local flux $\Phi_{re}$. $\Phi_{re}$ is an additional flux provided by the resonator inductance that is added to the original transmit flux $\Phi_{rf}$. Therefore, the total flux $\Phi_t$ around the resonator can be written as:

$$\Phi_t = \left( \frac{R + iwL}{R + iwL + \frac{1}{iwC}} \right) \Phi_{rf} \qquad (1)$$

at resonance, when $$w = w_0 = \frac{1}{\sqrt{LC}},$$

$$\Phi_t = \left(1 + i\frac{wL}{R}\right)\Phi_{rf} = (1 + iQ)\Phi_{rf} = \Phi_{rf} + i\Phi_{re} \quad (2)$$

where i represents a quadrature phase relationship between the transmit flux and the flux generated by the resonator. Q is the resonator Q-factor.

The local flux generated by the resonator leads to an extra excitation field, which alters the effective FA by position. Based on the Lenz's law, the magnetic flux generated by the passive resonator is in opposite direction of the original flux, $\Phi_{rf}$, which may result in total flux, $\Phi_t$ cancelation at the very close vicinity of the resonator (e.g. at the center, where the flux generated by the resonator is strong). But at the outer side of the resonator $\Phi_t$ is amplified since the $\Phi_{re}$, and $\Phi_{rf}$ are in the same directions.

The fundamental signal in an MR experiment comes from the detection of the electromotive force (emf) for precessing magnetization, as disclosed in Marques, J. P., et al., "Cerebellar cortical layers: in vivo visualization with structural high-field-strength MR imaging," *Radiology*, 254(3):942-948 (2010), the disclosure of which is incorporated herein by reference in its entirety. The emf induced in the coil in our system can be expressed as:

$$\text{emf} = -\frac{d\phi}{dt} = -\int B_t(\vec{r}) \cdot M(\vec{r}, t) d^3r \quad (3)$$

where $B_t$ is the total magnetic field at a position (x,y,z) by unit current passing through the coil base on the principle of reciprocity, as disclosed in Raichle, M. E., "Images of the mind: Studies with modem imaging techniques," *Annual Review of Psychology*, 45(1), 333-356 (1994), the disclosure of which is incorporated herein by reference in its entirety. M is the magnetization vector.

According to the Faraday's law of induction, the nuclear magnetic resonance signal detected by the receiver coil in the presence of the RF resonator is:

$$S(t) \propto -\frac{d}{dt}\int B_t(\vec{r}) \cdot M(\vec{r}, t) d^3r \quad (4)$$

from Eq. 2, $B_t=(1+Q)B_{rf} \cong QB_{rf}$, therefore:

$$S(t) \propto -\frac{d}{dt}\int QB_{rf}(\vec{r}) \cdot M(\vec{r}, t) d^3r \quad (5)$$

Additional local magnetic field generated by the resonator increases the signal intensity near the resonator by the factor of ($\approx Q$). For an optimal signal enhancement the resonator normal axis should be in the same direction with the excitation filed. Tilting the resonator results in decreasing the coupling level, consequently signal amplification. In this study, the resonators are almost in maximum coupling position.

A commercially available Nova Medical 1Tx/32Rx birdcage head coil for RF transmission and MRI signal reception at 7 T was utilized. An array including 10 broadside-coupled split-ring-resonators (BCSRR) was placed inside the birdcage coil covering the base of the skull of the patient such that it extended 6 cm out from the coil.

Assuming a single BCSRR, the circularly-polarized transmit magnetic field, $B_{rf}$ of the transmit coil inductively couples to the resonator, the reaction of the resonator with excitation field leads to circulating current in the resonator, which results in a secondary magnetic field, $B_{re}$ in the resonator vicinity, as shown in FIG. 4C. Considering a circularly polarized magnetic field generated by the commercially available quadrature birdcage coil gives:

$$B_{rf}(t) = B_1^+(\cos wti - \sin wtj) \quad (6)$$

where $B_1^+$ is am amplitude modulation function and $w=2\pi f$ is the carrier frequency of the transmission. The inductive coupling between the resonator and $B_{rf}(t)$ results in a linearly polarized magnetic field ($B_{re}$) generated by a resonator, which can be expressed as:

$$B_{re}(t) = 2B_{re}^+ \cos wti \quad (7)$$

Assuming the angle between CP magnetic field lines and normal vector of the resonator is zero, therefore, from Faraday's law of induction, the electromotive force ($\varepsilon$) generated by $B_{rf}(t)$ is given:

$$\epsilon = -\frac{d\phi}{dt} = (\pi r^2) w B_1^+ \quad (8)$$

where r is the radius of the resonator. If the resonator is assumed as a series RLC circuit, the input impedance can be written as:

$$Z_{re} = R\left[1 + i\frac{wL}{R}\left(\frac{f^2 - f_0^2}{f^2}\right)\right] \quad (9)$$

where R represents the ohmic losses, L is the resonator inductance, $f_0$ is the resonance frequency of the resonator, $Q=wL/R$ is the resonator Q-factor, and $f=1/2\pi\sqrt{LC}$ is the actual detuning frequency of the resonator. Assuming $\Delta f = (f-f_0)$ and considering $\Delta f$ is relatively small compared to $f_0$ the impedance can be simplified to:

$$Z_{re} = R\left[1 + i2\frac{wL}{R}\left(\frac{\Delta f}{f_0}\right)\right] \quad (10)$$

The associated ohmic loss, R, is typically small, therefore the induced current on the resonator can be written as:

$$I_{re} = \frac{\epsilon}{Z_{re}} \approx \frac{(\pi r^2) B_1^+}{L}\left(\frac{f_0}{\Delta f}\right) \quad (11)$$

The modulation magnetic field generated by the induced current at distance z away from the resonator center is given by:

$$B_{re}(t) \approx \frac{\mu(\pi r^2) B_1^+}{L\left(1 + \left(\frac{z}{r}\right)^2\right)^{\frac{3}{2}}}\left(\frac{f_0}{\Delta f}\right) \cos wti \quad (12)$$

This linearly polarized field decomposes into two circularly-polarized fields: (i) a circularly forward-polarized field and (ii) a circularly reverse-polarized field, which mathematically can be written as:

$$B_{re}(t) \simeq \frac{\mu(\pi r)B_1^+}{2L\left(1+\left(\frac{z}{r}\right)^2\right)^{\frac{3}{2}}}\left(\frac{f_0}{\Delta f}\right)[\cos wti - \sin wtj] + \qquad (13)$$

$$\frac{\mu(\pi r)B_1^+}{2L\left(1+\left(\frac{z}{r}\right)^2\right)^{\frac{3}{2}}}\left(\frac{f_0}{\Delta f}\right)[\cos wti + \sin wtj]$$

The first term represents the circularly forward-polarized field and the second one represents the circularly reverse-polarized field. The second term, which has a negligible effect on the spin excitation, can be neglected and only the forward-polarized field is considered, which is more resonant with the spins and rotates in the same direction as the recessing spins.

Therefore, the total magnetic field at the distance z from the resonator center is:

$$B_1^+(t) \simeq B_{rf}(t) + \frac{\mu\pi B_1^+}{2L\left(1+\left(\frac{z}{r}\right)^2\right)^{\frac{3}{2}}}\left(\frac{f_0}{\Delta f}\right)[\cos wti - \sin wtj] = \qquad (14)$$

$$\left[1+\frac{\mu\pi}{2L\left(1+\left(\frac{z}{r}\right)^2\right)^{\frac{3}{2}}}\left(\frac{f_0}{\Delta f}\right)\right]B_1^+[\cos wti - \sin wtj]$$

where $B_1^+$ is the original magnitude of $B_1^+(t)$, when there is no resonator in place. Considering a resonator tuned below the Larmor frequency (f>$f_0$), then the total magnetic field, $B_1^+$ can be cancelled in the region effected by the resonator. Therefore, the desired off-resonance frequency, f should be above the Larmor frequency to enhance the transmit field. In general, transmit field efficiency is lower at the inferior region of the coil and higher compensation may be required. The off-resonance frequency was adjusted 5% above the Larmor frequency to obtain optimized transmit efficiency in the presence of the resonator. The coupling between the resonator and the birdcage coil depends on the resonator orientation relative to the coil. Therefore, the transmit field profile of the resonator, $B_{re}$ depends on its relative orientation to the coil.

Inductive coupling of an array of resonators with the birdcage coil is more complicated than a coupling of a single resonator. All of the array elements are inductively coupled through the birdcage coil, therefore their interaction is considered well in global homogenization. To this end, full-wave electromagnetic simulations were performed for more complementary results.

Example 4—Radiofrequency Resonator Modeling

A single radiofrequency (RF) resonator was simulated as a circular coupled-split-ring resonator (CSRR), as disclosed in Alipour, A., et al., "Sensitivity Enhancement at 7 T Brain MR imaging Using Wireless Coupled-Split-Ring-Resonators Array," International society of magnetic resonance imaging, 37 (2020), the disclosure of which is incorporated by reference herein in its entirety. The CSRR is a 3-layer structure; a flexible dielectric substrate ($\varepsilon_r$=3.4) which is sandwiched between two Split-Ring Resonators (SRRs); the SRRs are 180°-rotated version (anti-oriented) of each other as shown in FIG. 5A. The SRR is an enclosed metal loop with a gap (g) along the loop.

When tuning a resonator, it is desirable to control the capacitance to reach the Larmor frequency, $f_{Lar}$, as disclosed in Alipour, A., et al., "Sensitivity Enhancement at 7 T Brain MR imaging Using Wireless Coupled-Split-Ring-Resonators Array," International society of magnetic resonance imaging, 37 (2020); 37. Alipour, A., "An inductively coupled ultra-thin, flexible, and passive RF resonator for MRI marking and guiding purposes: Clinical feasibility," Magn Reson Med, 80(1):361-370 (2018); and Gokyar, S., et al., "Magnetic Resonance Imaging Assisted by Wireless Passive Implantable Fiducial e-Markers," Access, 5:19693-19702 (2017), the disclosures of which are incorporated by reference herein in their entirety. The built in distributed capacitance between the metal layers in the CSRR structure are used to tune the resonator to $f_{Lar}$ and avoids the need for any lumped element capacitance.

An equivalent circuit model of a CSRR is shown in FIG. 5B, where the resonator is modeled as a series RLC circuit with distributed capacitance and mutual coupling between the layers. Resonance frequency and Q-factor of a resonator are given by Equation (15) and Equation (16), respectively.

$$w_0 = \frac{1}{\sqrt{L_e C_e}} \qquad (15)$$

$$Q = \frac{wL_e}{R_e} \qquad (16)$$

where $L_e$ is the effective inductance, $R_e$ is an AC resistance of the structure, and $C_e$ is the effective capacitance of the overall structure. The approximate effective inductance, capacitance, and resistance of the given design can be formulated as disclosed in Marques, J. P., et al., "On the origin of the MR image phase contrast: an in vivo MR microscopy study of the rat brain at 14.1 T," Neuroimage, 46(2):345-352 (2009), the disclosure of which is incorporated herein by reference in its entirety:

$$L_e = 2.54\mu D\left[\ln\left(\frac{2.07}{\rho}\right) + 0.18\rho + 0.13\rho^2\right] \qquad (17)$$

$$C_e = \varepsilon_0 \varepsilon_r \frac{A}{d} \qquad (18)$$

$$R_e = \frac{2l}{T\sigma\delta(1-e^{-b/\delta})} \qquad (19)$$

where $\mu$ is the permeability of the copper, D is the average diameter (D=(($D_o$+$D_i$)/2), $\rho$ is the fill ratio ($\rho$=($D_o$−$D_i$)/($D_o$+$D_i$)), $D_o$ is the outer diameter, $D_i$ is the inner diameter, $\varepsilon_0$ is the permittivity of the free space, $\varepsilon_r$ is the relative permittivity of the dielectric substrate, A is the parallel plate surface area, d is the distance between the consecutive layers (dielectric thickness), W is the metallization (copper) width, l is the path length of the metal trace, b is the copper thickness (35 µm), $\sigma$ is the conductivity of the copper, and $\delta$ is the skin-depth of the copper.

Electrical characteristics of the RF resonator rely on $L_e$, $R_e$, and $C_e$, which depend on four design parameters: (1) the average diameter D, (2) the dielectric thickness d, (3) gap g, and (4) the copper width W.

A series of EM simulations (Computer Simulation Technology Microwave Studio (CST), Germany) was performed to investigate the effects of design parameters on the electrical properties of a single CSRR. Optimized resonator geometry was used for the array modeling.

Example 5—RF Array Modeling

Figure 6:
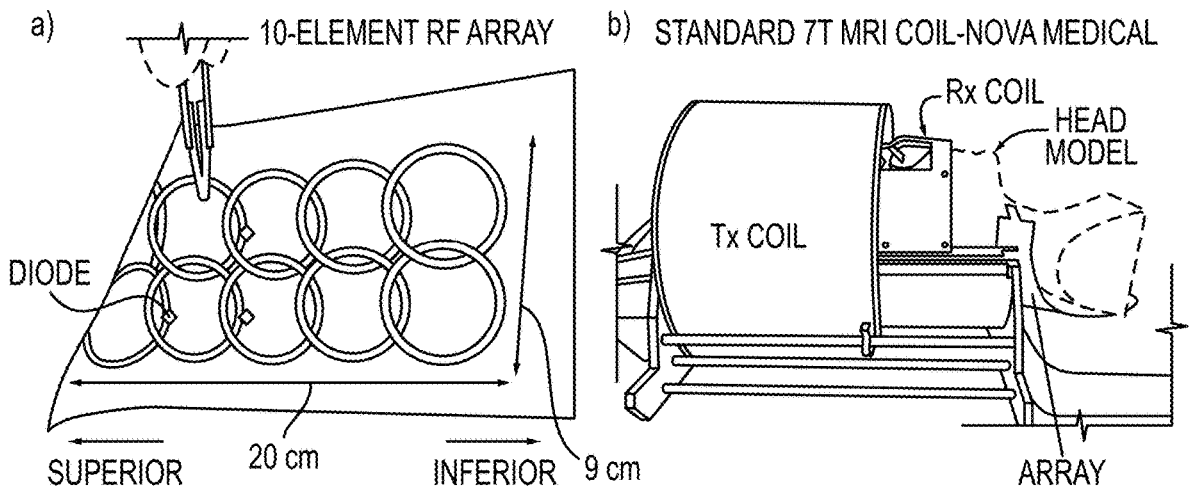
FIG. 6A illustrates a prototype of the 10-element wireless passive RF resonator array constructed of 10 CSRRs. 10 SRRs are patterned on one side of the flexible substrate (Kapton), then after 10 anti-oriented version of these SRRs were patterned on the other side of the substrate to complete the CSRRs structure. The resonators were decoupled from each other using critical overlap technique.
FIG. 6B illustrates a picture of a standard head coil used in the MRI experiments and the position of the array relative to the coil and head phantom model.

A 10-element wireless passive RF resonator array was designed using 10 resonators (CSRRs) as shown in FIG. 6A. The elements were aligned in a form of a 2×5 matrix. The critical overlap technique was used to decouple adjacent elements, as disclosed in Adriany, G., et al., "A half-volume coil for efficient proton decoupling in humans at 4 tesla," *J Magn Reson,* 125(1):178-184 (1997), the disclosure of which is incorporated by reference herein in its entirety. EM numerical simulations (CST) were conducted to evaluate the EM field distribution of a head coil in the presence of the RF array. A head-sized quadrature-driven high-pass birdcage coil (22 cm in diameter and 25 cm in length) was modeled, similar to the transmit head coil used in the experiments. The coil had 12 rungs connected at each end to two end rings and shielded by an open cylinder (23 cm in diameter and 27 cm in length). The coil was excited at two rungs, 90° apart in position and single phase, generating a circularly-polarized excitation. The coil was tuned by lumped capacitors distributed at the end-ring gaps and matched to 50Ω using a single capacitor at each port, placed in series with an ideal voltage source with a 50Ω internal resistance. For the simulation, the input power of the coil was adjusted to produce 1 W total power and a mean $B_1^+$ of 13 µT inside the head on an axial plane passing through the center of the coil. The performance of the 10-element RF resonator array was evaluated on a head model. The array was placed between the coil and the phantom: 3 cm away from the coil and 1 cm away from the phantom.

To calculate the maximum 10 gr local average SAR values via simulation, we loaded the coil with a head model. The array was placed at the posterior position, between the head and the coil as shown in FIG. 6B. RF excitation was performed using a birdcage head coil. Simulations were performed for both with and without the array. Numerical SAR results were acquired using a time domain solver and a power-loss monitor. Time-averaged SAR values were calculated by finding the time derivative of the incremental energy, absorbed by an incremental 10 g mass of tissue. All resulting simulated SAR values were compared with the corresponding limits (10 W/kg for maximum local SAR and 3.2 W/kg for head average SAR) recommended by the FDA and IEC, as disclosed in the FDA's Aug. 2, 2019 guidance entitled Testing and Labeling Medical Devices for Safety in the Magnetic Resonance (MR) Environment, the disclosure of which is incorporated herein by reference in its entirety.

Example 6—Fabrication

A single RF resonator was fabricated using the preferred design parameters found in the EM simulations. Parameter optimization was performed to obtain efficient electrical characteristics. The CSRR is a multilayer laminated structure including two anti-oriented coupled SRRs, which are patterned on both sides of the dielectric substrate as shown in FIG. Ba. The fabrication processes include the following steps: (1) a copper layer of SRR was patterned on one side of a flexible dielectric substrate (Kapton® polyimide films, DuPont™); (2) a copper layer of SRR with 1800 rotation was patterned on the other side of the substrate in the same axis with the first layer. The array was constructed using resonators with the following design parameters: $D_o$=50 mm, $D_i$=44 mm, D=47 mm, ρ=0.064, d=100 µm, T=3 mm, g=20°, l=152 mm, A=444 mm².

For RF array fabrication, 10 SRRs (first layer) were patterned on one side of a single piece of a dielectric substrate (Kapton), and then patterning 10 more SRRs (second layer) on the other side of the substrate completed the process. Second SRRs are in the same axis with first SRRs but with 1800 rotation (anti-oriented). The total dimension of the array is 9 cm×20 cm as shown in FIG. 6A. The critical overlapping between neighboring elements serves to reduce the inductive coupling between elements. The overlap is based on the critical loop center-to-center distance to minimize mutual inductance.

The built in distributed capacitance between two layers in a single CSRR was used for fine frequency tuning. Changing the conductor length can affect the capacitance and inductance values, consequently the operator frequency.

In order to prevent the over-flipping of the RF excitation and avoid boosting the absorption RF energy, some of the resonators were decoupled from RF excitation, specifically the resonators, which were in strong coupling position with RF excitation. The circuit model of a decoupled resonator is shown in FIG. 5A The coupling level was evaluated using a $B_1^+$ mapping method, as described below. An antiparallel diode (Macom, Newport Beach, CA, USA) passively detuned the resonators during RF transmission.

Example 7—Electrical Bench Test

All elements were tuned to the Larmor frequency ($f_0$) at 7 T (297 MHz) while loaded with the cylindrical saline phantom (15 cm in diameter and 30 cm in height; dielectric constant: 75; conductivity: 0.60 s/m). A foam pad (0.3 cm thick and $\varepsilon_o$=2.1) was placed between the array and the phantom to keep the same conditions as MRI experiments. Resonance frequency and Q-factor were assessed by measurements the S-parameters using a double pickup probe in a vector network analyzer (E5071C, Agilent Technologies, Santa Clara, CA, USA). Q-factor was calculated as a ration of a resonance center frequency to FWHM bandwidth in the transmission coefficient ($S_{21}$). Detuning performance of the resonators (detuned with antiparallel diode) was measured as the change in the $S_{21}$ of a double pickup probe. Decoupling between array elements was examined by $S_{21}$ measurements between the pairs of elements.

Example 8—Experimental Safety Analysis

To evaluate the effect of the RF resonator array in SAR distribution, temperature measurements were conducted in the vicinity of the array in an MRI scanner. The RF array was placed on top of a gel phantom (rectangle: 15 cm×20 cm, $\delta_{gel}$=0.6 S/m, $\varepsilon g_{ei}$=77), where a thin layer of plastic was used to avoid the direct contact of the array with the gel. The assembly was placed inside the head coil and was scanned for 15 min with a high SAR turbo-spin-echo (TSE) sequence (repetition-time (TR)=1500 ms, echo-time (TE)=8 ms, Flip-angle (FA)=120°, bandwidth=977 Hz/pixel, field-of-view (FOV)=16×23 cm2, matrix=128×128). RF excitation was performed using a Nova1Tx/32Rx head coil (Nova Medical, Wilmington, MA) in a 7 T MRI scanner (Magnetom, Siemens Healthcare, Erlangen, Germany). Temperature was measured using four fiber-optic temperature probes (Luma-Sense Technologies, Santa Clara, CA) located at the high SAR value expected spots in the vicinity of the array. The temperature of a reference point far from the array was also collected. Baseline temperatures were recorded before RF transmission, and temperature changes were measured during scanning.

For the control experiment, which had no RF array, the local temperature rises at the temperature probe locations was determined. The probes were placed at the same spatial positions. SAR was calculated as:

$$SAR = C\frac{dT}{dt} \quad (20)$$

where C is the heat capacity, T is the temperature and t is the time.

The location of the probes was visually examined relative to the RF array, immediately before and also after the heating assessment because significant variations in the measured temperature can occur due to slight variations in the probe positions relative to the array. Therefore, the exact same location of the probe was used when studying the temperature changes occurring with and without the array.

Example 9—Phantom MR Experiment

The phantom (CuSo4 solution) MR experiments were conducted to evaluate the array performance by characterizing the image SNR. The flexible and thin structure of the array allows the array to be placed on the curved surfaces to fully cover the interested region. All images were obtained on a 7 T MR scanner using Nova1Tx/32Rx head coil. GRE (TR=400 ms, TE=4 ms, FA=10°, bandwidth=977 Hz/pixel, FOV=16×21 cm2, matrix=128×128) sequences were used to compare the images acquired with and without the RF array. The combined system (commercial Nova 1Tx/32Rx head coil in combination with the 10-element RF resonator array) performance was compared with a conventional Nova1Tx/32Rx head coil as a reference. SNR mapping was performed by obtaining two images with/without RF excitations, and then it was normalized by $B_1^+$ to isolate the receive sensitivity from the transmit field distribution.

The effect of the RF resonator array in transmit RF efficiency was also evaluated by mapping the $B_1^+$ field produced in the phantom using the double angle method. $B_1^+$ distribution was used to determine the coupling level between the coil and individual resonators.

The birdcage coil was not re-tuned and re-matched in the presence of the RF array, as tuning and matching were fixed for the commercial coil used in the experiments.

Example 10—Ex-Vivo MR Imaging

The ex-vivo MR imaging was performed in three cadaver brains (Musk Ox). The brains were fixed inside a cylindrical (12 cm in diameter and 16 cm in length) formalin-filled (400 mL of 10% neutral buffered formalin) container. The assembly was then vacuumed for 30 min to remove the bobbles.

The brains were imaged on a whole-body 7 T MRI scanner (Magnetom, Siemens Healthcare, Erlangen, Germany) using a single channel transmit and 32-channel receive (1Tx/32Rx) Nova head coil.

The RF array was placed at the posterior position of the head coil and the brain-contained container seated over the array. A foam pad with a thickness of 0.3 cm was used as an outer cover layer for the array.

MR images with and without RF array were obtained using GRE sequences (TR=400 ms, TE=4 ms, FA=10°, bandwidth=977 Hz/pixel, FOV=16×21 cm2, matrix=128× 128). Following this, high-resolution T1-weighted MP-RAGE sequences (TR=400 ms, TE=4 ms, FA=10°, bandwidth=977 Hz/pixel, FOV=16×21 cm2, matrix=128× 128) were applied. Proton density TSE sequences (TR=400 ms, TE=4 ms, FA=10°, bandwidth=977 Hz/pixel, FOV=16× 21 cm2, matrix=128×128) were also applied to assess the performance of the proposed RF array under various MRI sequences.

Ex-vivo contrast enhancement analysis was also performed using calculation of contrast-to-noise ratio (CNR). CNR was calculated as:

$$CNR = \left|\frac{S_{ROI} - S_{REF}}{\sigma_N}\right| \quad (21)$$

where $S_{ROI}$ and $S_{REF}$ are the signal intensities of the region-of-interest (ROI) and reference point, respectively. $\sigma_N$ is the standard deviation of noise.

Example 9—Results: Resonator Modeling

The inductive coupling between the transmit magnetic field and the RF resonator generates an additional magnetic field that manipulates the total magnetic field. In addition, in the receive phase, coupling between the magnetization vector and the resonator enhances MR signal. The resonator inductance, $L_e$ plays a main role in coupling levels.

Figure 7:
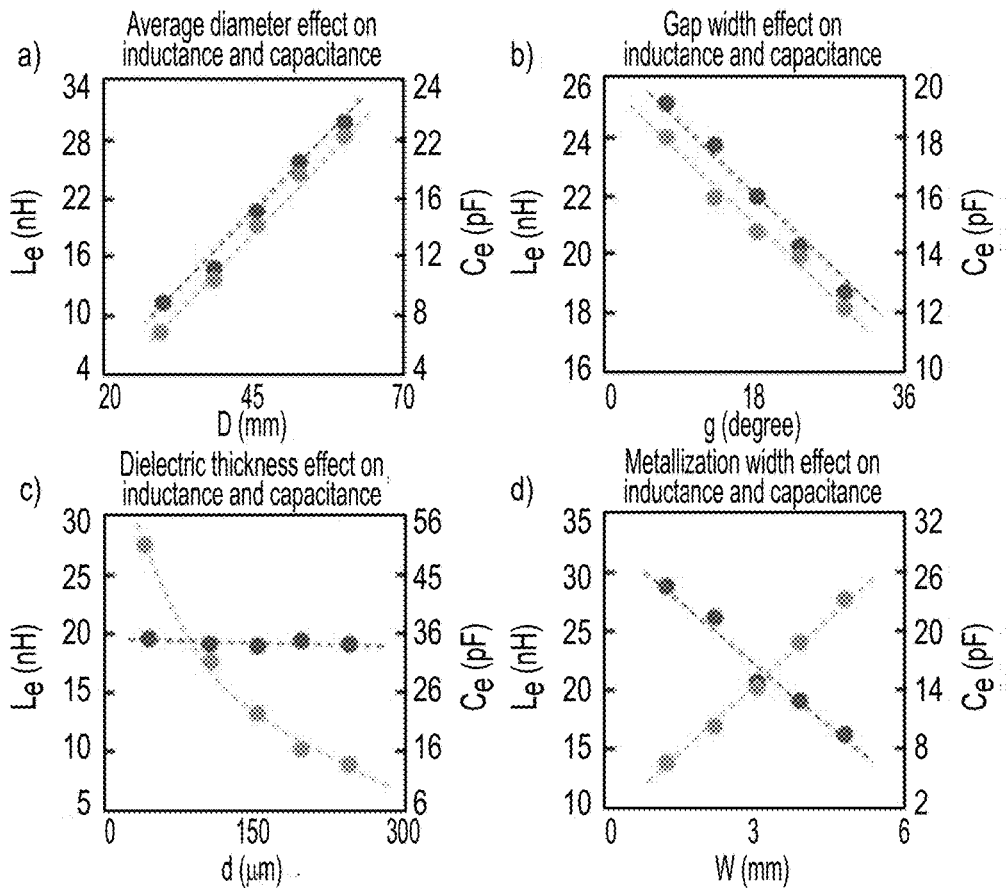
FIG. 7A illustrates EM simulation results detailing the effect of gap width ($g=6°, 12°, 18°, 24°$, and $30°$) with D, W, and d kept constant ($D\backslash W=47\backslash 3$ mm, $d=200$ μm); the $L_e$ and $C_e$ decreased with g.
FIG. 7B illustrates EM simulation results detailing the effect of average diameter ($D=27, 37, 47, 57, 67$) with other parameters ($W=3$ mm, $d=$μm 200, and $g=18°$) kept constant. As D increased, the $L_e$ and $C_e$ increased due to increasing conductor length and overlap region.
FIG. 7C illustrates EM simulation results detailing the effect of metallization width ($W=1, 2, 3, 4$, and 5 mm). The $L_e$ decreased because of larger conductor cross-section and $c_e$ increased due to increasing overlap area as the metallization width increases, with other parameters kept constant ($D=47$ mm, $g=18°$, $d=200$ μm).
FIG. 7D illustrates EM simulation results detailing the effect of dielectric thickness ($d=50, 100, 150, 200$, and 250 m) with $D\backslash W=47\backslash 3$ mm, $g=18°$. The $c_e$ decreased as it is proportional with the inverse of dielectric thickness. $L_e$ was not changed with d variations.

The overlapping area (A) and conductor length (l) are the major determinants in the $L_e$ and $C_e$ values of the resonator, which are controlled by the design parameters D, W, g, and d values. The effect of design parameters was numerically analyzed for different D, W, g, and d values. Results for five average diameter (D) values, with d, g, and W kept constant d=200 µm, g/W=20/3 mm), showed that $L_e$ and $C_e$ were increased as D increased, as shown in FIG. 7A. The average diameter increasing is associated with extending the A and I, which results in increased $L_e$ and $C_e$ values, respectively.

The gap width (g) effect was studied with other parameters kept constant (d=200 µm, D/W=47/3 mm). As g increased both $L_e$ and $C_e$ decreased, since the A and I decreased, as shown in FIG. 7B.

The dielectric thickness (d) effect was evaluated, with D, g, and T kept constant (D/g/W=47/20/3 mm). The effective capacitance $C_e$ decreased by increasing d, as the capacitance value is inversely proportional with the dielectric thickness, as shown in FIG. 7C. The effective inductance $L_e$ did not show a significant change by d variations.

Results for conductor width (W) as the other parameters keep constant (d=200 µm, D/g=47/20), showed that $C_e$ increased and $L_e$ decreased as W increased, as shown in FIG. 7D. Increasing W results in higher overlapping area, consequently higher $C_e$ values. On the other hand, increasing W leads larger conductor cross-section for electrical charge flow, which resulted in lower $L_e$ values.

Figure 8:
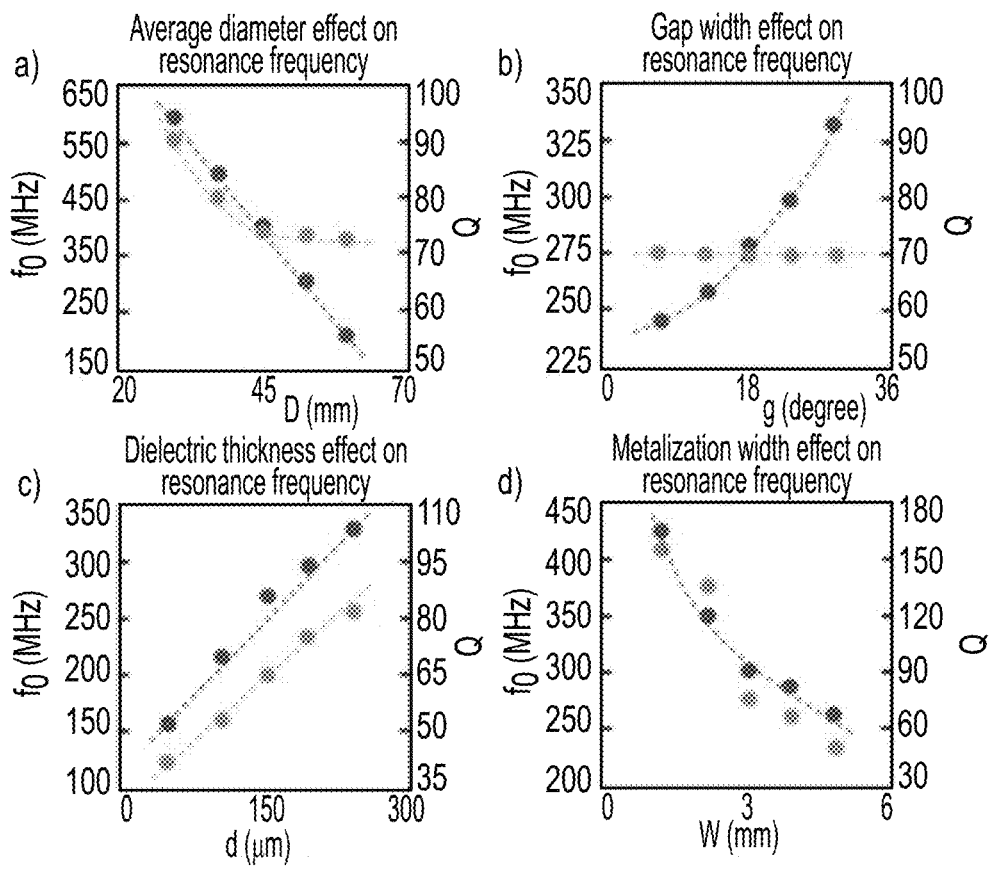
FIG. 8A illustrates EM simulation results detailing effects of the parameter D on the resonator resonance frequency ($f_0$) and Q-factor. $f_0$ decreased as D increased, which can be explained by the dominant effect of increased $L_e$. Q showed an exponential decreasing behavior as D increased.
FIG. 8B illustrates EM simulation results detailing effects of the parameter g on the resonator resonance frequency ($f_0$) and Q-factor. $f_0$ exponentially increased and Q did not change as g increased.
FIG. 8C illustrates EM simulation results detailing effects of the parameter d on the resonator resonance frequency ($f_0$) and Q-factor. $f_0$ and Q linearly increased as d increased.
FIG. 8D illustrates EM simulation results detailing effects of the parameter W on the resonator resonance frequency ($f_0$) and Q-factor. $f_0$ showed an exponential decreasing behavior by increasing W and Q randomly was decreased as W increased.

Similar analyses were performed to evaluate the effect of the design parameters on resonance frequency ($f_0$) and Q-factor (Q), as shown in FIGS. 8A-8D. EM simulation results detailing effects of the parameters g, D, W, and d on the resonator resonance frequency ($f_0$) and Q-factor. During each parameter evaluation, the other parameters were kept constant. Increasing the $L_e$ and $C_e$ by increasing D resulted in decreasing $f_0$, as shown in FIG. 8A. Q decreased exponentially as D increased, which can be explained by the dominant effect of frequency decreasing. $f_0$ exponentially increased by increasing D, as shown in FIG. 8B, since $L_e$ and $C_e$ were decreased. Q was not affected by D variations. $f_o$ and Q linearly increased as d increased, as shown in FIG. 8C, which can be explained by decreasing $L_e$. $f_0$ exponentially decreased as W increased, as shown in FIG. 8D, because of the dominant effect of decreased $L_e$. Q also decreased by increasing W. During studying each parameter, the other parameters were keep constant.

The following design parameters were used in 10-element array construction to have an efficient performance: $D_o$=50 mm, $D_i$=44 mm, D=47 mm, ρ=0.064, d=200 μm, T=3 mm, g=30°, l=132 mm. These parameters were selected based on: (a) optimized Q; to have sufficient signal enhancement and avoid signal saturation, (b) RF resonator size; keeping the size big enough to avoid wavelength effect.

Example 11—RF Array EM Simulation

A 10-element (2×5) RF array was simulated, where the elements were decoupled from each other using critical overlapping method. The mutual coupling between elements is minimized and the resonators are decoupled when yy=0.76 DD. Simulated scattering (S) parameters of the decoupled resonator pair show a transmission coefficient $S_{21}$ of −24 dB at 300 MHz.

In the presence of the 10-element RF array, simulated S parameters of the transmit coil (birdcage) show no significant changes in reflected and forward power. $S_{11}$ and $S_{22}$ remained below −22 dB and $S_{21}$ value showed an insignificant increase about 1% in transmitted power. The birdcage head coil was not re-matched and re-tuned due to these negligible changes in S parameters. The simulation results showed improved $B_1$ efficiency at the regions covered by the array. $B_1^+$ was enhanced up 2-fold in the brain, as compared to the case without the array. The RF array resulted in 2-fold improvement in transmit efficiency in the cerebellum and 27% decrease in the coil center. Maximum 10 gr local and average SAR values were simulated using the human model from the library of the CST. SAR distribution was computed in the birdcage coil in the presence of the array. The results showed that the local SAR increased from 1.32 to 1.76 W/kg and average SAR increased from 0.88 to 1.12 W/kg. FDA and IEC recommended corresponding limits for maximum local SAR is 10 W/kg and for head average SAR is 3.2 W/kg. All computed SAR values were well below theses limits.

Example 12—Bench-Top Measurements

Although the required design can be achieved through a simulation analysis, it can also be tuned on the bench-top based on $S_{11}$ and $S_{21}$ measurements. Specifically, to obtain the minimum decoupling condition, y should be adjusted such that the frequency with minimum $S_{21}$ is equal to the $f_0$.

Figure 9:
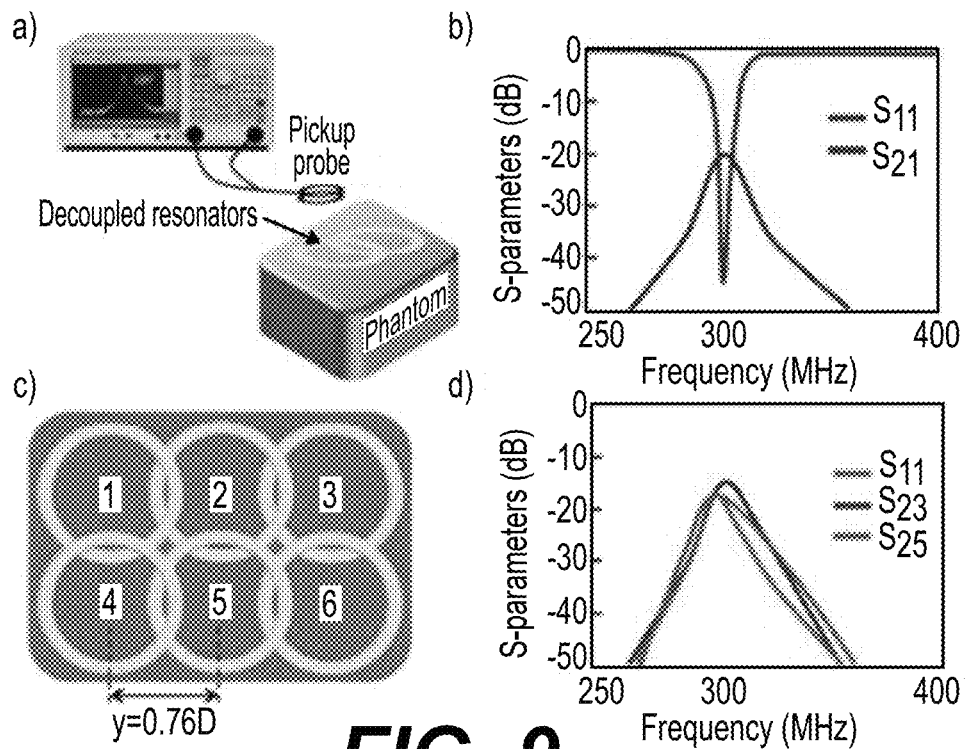
FIG. 9A illustrates a bench test setup to measure the coupling between two resonators.
FIG. 9B illustrates measured S-parameters for two decoupled resonators (center-to-center distance=0.76D, D is the average ring diameter). $S_{21}$ shows about −20 dB decoupling level, the symmetric behavior of $S_{11}$ also proves the fact.
FIG. 9C is a schematic of the array to show the various coupling modes. All the elements were separated by critical overlapping technique (y=0.76D).
FIG. 9D illustrates measured S-parameters showing the coupling values of the resonator number 2 with two other resonators in the same raw (numbers 1 and 3) and in the same column (number 5). Measured $S_{21}$, $S_{23}$, and $S_{25}$ show coupling values bellow −15 dB.

An array of two decoupled resonators with the same size as the simulated array in Example 9 is shown in FIG. 9A illustrating the bench-top experiments used for S-parameter measurements plotted in FIG. 9B. As expected, the critically overlapped (y=0.76 D) resonators are strongly decoupled from each other, with a transmission coefficient $S_{21}$ of −19 dB. The strong decoupling also makes the reflection coefficient ($S_{11}$) plot symmetrical around the $f_0$.

A 10-element array consisted of 10 resonators (2 columns and 5 rows) was further built in which two kinds of coupling exist between the elements: coupling between neighboring elements of the same row and coupling between neighboring elements of different rows, as shown in FIG. 9C. The same overlapping distance as 2-element (y=0.76 D) is used to decouple the resonators from different rows. Decoupling between elements was examined in the presence of the phantom by $S_{21}$ measurements between pairs of elements while all other neighboring elements were detuned using antiparallel diode.

In the array construction, resonator overlaps were adjusted to achieve acceptable decoupling level (<−15 dB) between elements in different rows, as shown in FIG. 9D.

The loaded Q-factor for the resonators was calculated as: $f_0/\Delta f$, where $\Delta f$ is the FWHM bandwidth of the measured $S_{21}$. The average loaded Q-factor of 21 was calculated.

The effect of bending on the 2-element array by 30° was also tested. Bending the array in the middle did not significantly change the S-parameters.

Example 12—Heating Experiment

After 15 min of RF transmission, a maximum temperature increase of 0.7° C. was experienced at the capacitive region (P2) of the resonator relative to the counterpart point in control (without array) set up. This resonator was strongly decoupled with the RF excitation (i.e., it was not detuned using antiparallel diode). Corresponding SAR gain of 1.2 was calculated. Other points recorded almost identical temperature increases.

The temperature increases were normalized relative to the reference point temperature. The temperatures at each position remained at raised levels for several minutes after RF transmission was turned off. This specifies that thermal convection in the gel was low, which suggests that the gel experiment overestimated in-vivo vascular conditions, where blood-flow leads to faster convective cooling.

Example 13—Phantom MRI

Experimental calculations in phantom demonstrated an overall SNR distribution variation in the presence of the RF array. The array resulted in 3-fold SNR enhancement in the region-of-interest (ROI, outlined in white). SNR maps normalized by the excitation FA maps resulted in a 7.2% reduction in the receive-only SNR in ROI, suggesting that the improvement in the SNR is primarily due to the increase in the FA (by 38.6%) with RF array.

The spatial distribution of the FA maps ($B_1^+$ maps) in the experiments indicated a similar trend to simulations, with improved performance toward the inferior region when the RF array is present. The FA averaged across all subjects showed a mean improvement of 170% in the peripheral region and a decrease of 30% at the center, while the average FA in the phantom remained approximately the same.

Example 14—Ex-Vivo Brain MRI

Figure 10:
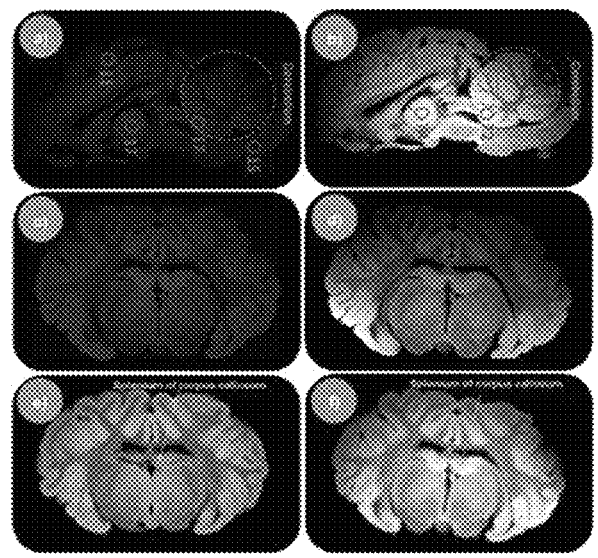
FIGS. 10A-10D illustrate ex-vivo MR imaging using different sequences. The images in the first column (FIGS. 10A-10C) were obtained without the array and the images in the second column (FIGS. 10E-10F) were obtained with the array. Images were archived on 7 T MRI scanner using a Nova 1-channel transmit and 32-channel receive (1Tx/32Rx) coil. Cadaver musk ox brains were used as the ex-vivo imaging model. Sagittal small tip angle GRE without array image (FIG. 10A) versus with array image (FIG. 10D) show significant SNR and contrast enhancement in the whole-brain when using the array. In particular, skull base and cerebellum are more clearly visible in the presence of the array with about 4-fold SNR improvement. Numbers indicate the SNR values. Comparison of T1-weighted coronal MPRAGE images (FIGS. 10B and 10E) show signal and contrast improvement in the peripheral regions of the brain and thalamus when using the array. Proton density TSE images obtained without (FIG. 10C) and with (FIG. 10F) the array show signal enhancement of about 2-fold at the thalamus.

Proof of concept ex-vivo MRI experiment at 7 T was conducted on 3 cadaver brains using a Nova 1Tx/32Rx head coil in conjunction with our proposed 10-element inductively coupled RF resonator arrays. Images obtained using GRE sequences indicate significant improvement in SNR at the brain, particularly in the skull base and cerebellum, as shown in FIGS. 10A and 10B (numbers indicate the SNR values). High-resolution MP-RAGE images obtained in the presence of the RF array resulted in 2-fold SNR enhancement at the thalamus, as shown in FIGS. 10C and 10D. The proton density TSE images show up to 90% SNR improved at the thalamus and peripheral regions in the presence of the RF array, as shown in FIGS. 10E and 10F.

The analysis of the CNR in the ROI indicated that contrast is enhanced on all images in the presence of the array. As shown in FIGS. 10A-10F, RF array resulted in 87% contrast enhancement on GRE images, 87% on MP-RAGE images, and 78% on proton density TSE images.

Example 15—In Vivo MRI at 7 T Using the Passive RF Resonator Array

In vivo MRI feasibility of the RF array was studied in five human subjects using TSE and GRE sequences. The array was placed behind the neck covering the posterior fossa, where the $B_1^+$ efficiency and signal sensitivity are intrinsically poor. FIGS. 11A and 11B show the sagittal T2-weighted TSE images improved visibility of the cerebellum, brainstem, and cervical vertebrae (dashed circle) in the presence of the RF array. Also, in FIG. 12, the axial T1-weighted GRE images obtained with and without the array focusing on posterior fossa show that the presence of the array improves the image uniformity and visibility of the cerebellum and the brainstem.

Figure 11:
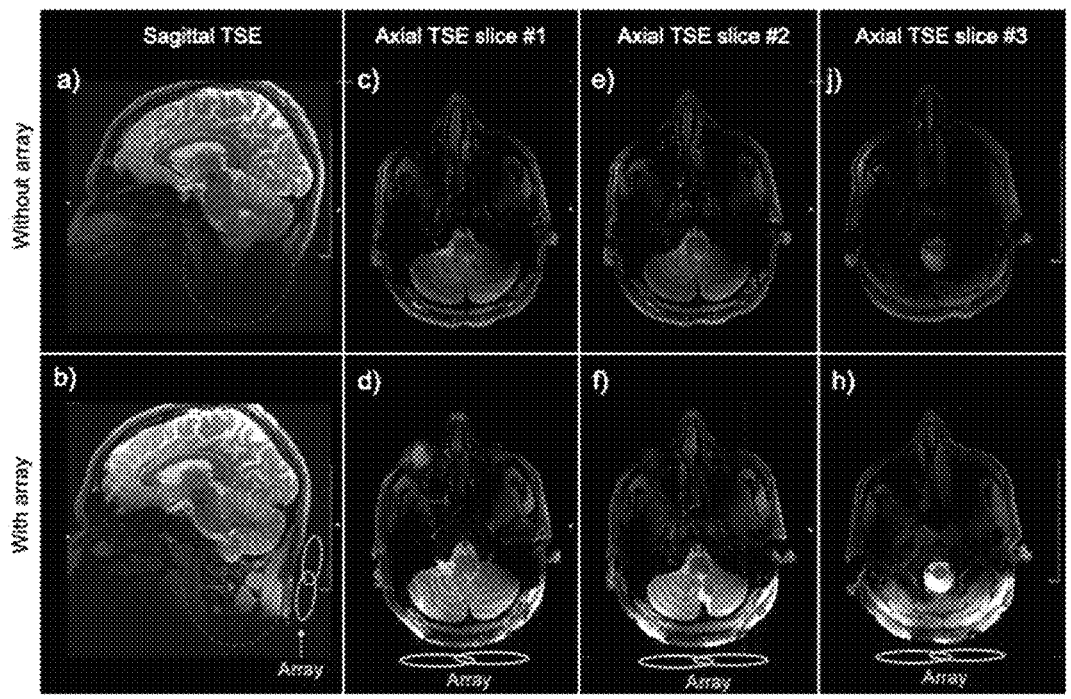
FIGS. 11A-11G illustrate images from an in vivo brain MRI at 7 T. Sagittal T2-weighted TSE images obtained without (FIG. 11A) and with (FIG. 11B) the RF array show significant SNR and CNR improvement in the inferior regions in the presence of the array. In particular, the cerebellum, brainstem, and neck muscle are more clearly visible using the RF array. Axial T2-Weighted TSE slices obtained at various locations in the lower brain are illustrated in FIGS. 11C-11G. Images obtained in slice #1 (FIGS. 11 and 11D) show that placing the RF array results in significant improvement in $B_1^+$ uniformity and SNR in the cerebellum and brainstem. Slice #2 (FIGS. 11E and 11F) and slice #3 (FIGS. 11G and 11H) obtained at the physical border and 2 cm extended outside of the border, respectively. These images show that using the RF array extends the anatomical coverage of the head coil visualizing vertebral artery and spinal cord, which are hardly visible without the array.
Figure 12:
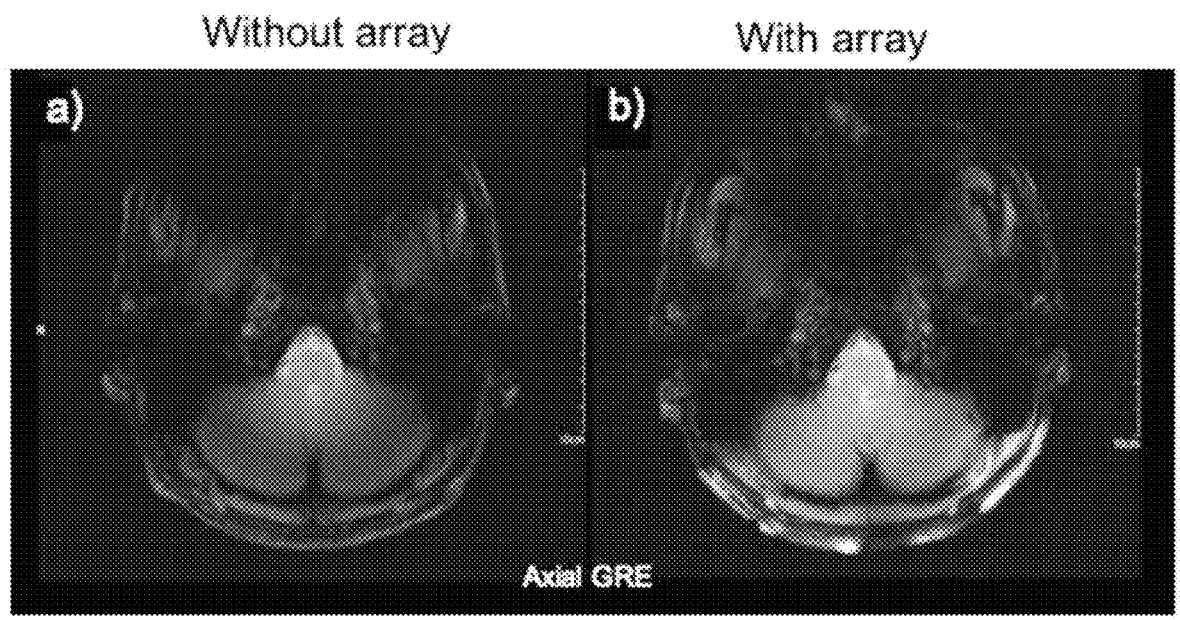
FIGS. 12A and 12B illustrate images from an in vivo brain MRI at 7 T. Axial GRE images obtained without (FIG. 12A) and with (FIG. 12B) the RF array show significant SNR and CNR improvement in the inferior regions in the presence of the array. In particular, the cerebellum, brainstem, and neck muscle are more clearly visible using the RF array.

FIG. 11 also shows the axial $T_2$-weighted TSE images obtained at various slices locating at the lower brain without and with the RF array shown. Slice #1 (FIGS. 11C and 11D) includes images focusing on the posterior fossa demonstrating significant $B_1^+$ efficiency and SNR enhancement in this region. Slice #2 (FIGS. 11E and 11F) and Slice #3 (FIGS. 11I and 11J) are images obtained approximately at the physical border of the coil and 2 cm away from the border (extended out in the MRI z direction), respectively. The presence of the array extends the spatial coverage of the coil allowing visualizing spinal cord and vertebral artery, which are barely detectable using the head coil without the array.

Axial TSE 0.7 mm in-plane resolution images of the cerebellum and brainstem demonstrate exquisite anatomical detail with excellent gray matter/white matter contrast. An average CNR enhancement of 52% and 58% between gray matter and white matter in the cerebellum was calculated in TSE and GRE images, respectively.

Figure 13:
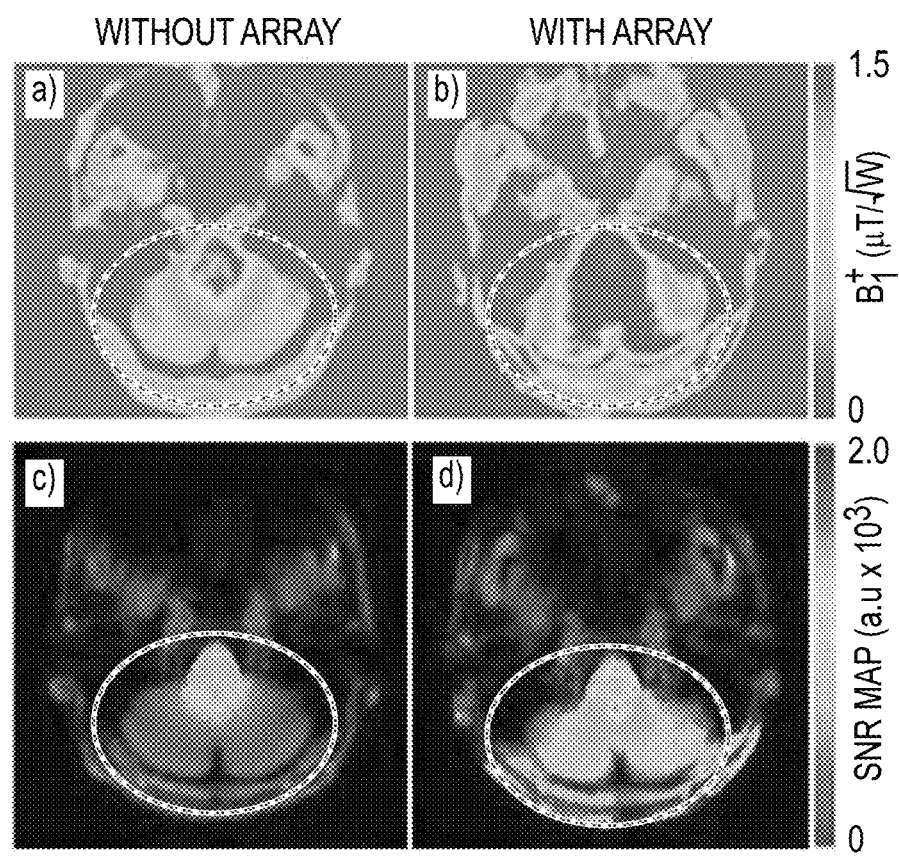
FIGS. 13A-13D illustrate experimental $B_1^+$ maps without (FIG. 13A) and with (FIG. 13B) the array show an improvement with the RF array in the inferior regions of the brain. Average $B_1^+$ enhancement of 1.8±0.2 was calculated across all subjects in the cerebellum and brainstem. Experimental SNR maps without (FIG. 13C) and with (FIG. 13) the array for one subject show that placing pads of the array at the back of the neck improves SNR in the cerebellum, neck muscles, and brainstem.

FIGS. 13A and 13B show measured in vivo axial transmit field ($B_1^+$) maps obtained with and without the RF array in one of the five human subjects. $B_1^+$ maps are calculated using the turbo-FLASH based method with the same input power. The average improvement factor of about 1.8±0.2 is measured over the ROI (dashed ellipse) in five human subjects.

FIGS. 13C and 13D show the experimental SNR maps without and in the presence of the RF array in the axial plane, respectively. The array improves the SNR by an average factor of 2.2 in the ROI including the cerebellum and brainstem.

Although preferred embodiments have been depicted and described in detail herein, it will be apparent to those skilled in the relevant art that various modifications, additions, substitutions, and the like can be made without departing from the spirit of the application and these are therefore considered to be within the scope of the application as defined in the claims which follow.

What is claimed is:

1. A radiofrequency resonator array device for use in magnetic resonance imaging (MRI) comprising:
   a substrate;
   an array of coupled split ring resonators located on the substrate, each of the coupled split ring resonators comprising:
   a first split ring resonator positioned on a first side of the substrate;
   a second split ring resonator positioned on a second side of the substrate located opposite the first side, the second split ring resonator coupled to the first split ring resonator, and wherein each of the coupled split ring resonators in the array of coupled split ring resonators are configured to generate a local radiofrequency field that increases resonator signal intensity near the coupled split ring resonator during operation of an MRI device.

2. A method of making a radiofrequency (RF) resonator array device for use in magnetic resonance imaging (MRI) comprising:
   providing a substrate;
   locating an array of coupled split ring resonators on the substrate, each of the coupled split ring resonators comprising:
   a first split ring resonator positioned on a first side of the substrate; and
   a second split ring resonator positioned on a second side of the substrate located opposite the first side, the second split ring resonator coupled to the first split ring resonator, and wherein each of the coupled split ring resonators in the array of coupled split ring resonators are configured to generate a local radiofrequency field that increases resonator signal intensity near the coupled split ring resonator during operation of an MRI device.

3. A method of generating a magnetic resonance image (MRI) using an MRI device, the method comprising:
   providing a radiofrequency (RF) resonator array device comprising:
   a substrate; and
   an array of coupled split ring resonators located on the substrate,
   each of the coupled split ring resonators comprising:
   a first split ring resonator positioned on a first side of the substrate; and
   a second split ring resonator positioned on a second side of the substrate located opposite the first side, the second split ring resonator coupled to the first split ring resonator, the second split ring resonator positioned in an orientation rotated 180 degrees with respect to the first split ring resonator, wherein each of the coupled split ring resonators in the array of coupled split ring resonators are configured to generate a local radiofrequency field that increases resonator signal intensity near the coupled split ring resonator during operation of the MRI device;
   positioning the RF resonator array device near a portion of a patient's anatomy to be imaged using the MRI device; and
   obtaining an MRI image of the portion of the patient's anatomy using the MRI device, wherein the RF resonator array device inductively couples to a magnetic coil of the MRI device during the obtaining to provide additional flux and amplify the receive MR signal during operation of the MRI device.

4. The device of claim 1, wherein the second split ring resonator is positioned in an orientation rotated 180 degrees with respect to the first split ring resonator.

5. The device of claim 1, wherein the substrate comprises a dielectric material.

6. The device of claim 1, wherein the substrate is constructed of a flexible material.

7. The device of claim 1, wherein the substrate has a thickness between about 50 micrometers and about 500 micrometers.

8. The device of claim 1, wherein the each of the coupled split ring resonators in the array of coupled split ring resonators are configured to inductively couple to a radiofrequency coil of the MRI device to provide additional flux during a transmit phase of the MRI device during operation of the MRI device.

9. The device of claim 1, wherein the each of the coupled split ring resonators in the array of coupled split ring resonators are configured to inductively couple to a radiofrequency coil of the MRI device to improve receive MR signal during a receive phase of the MRI device during operation of the MRI device.

10. The device of claim 1, wherein each of the coupled split ring resonators in the array of coupled split ring resonators is tuned to a resonance frequency that is equal to the Larmor frequency of the MRI device based on a field strength of the MRI device.

11. The device of claim 1, wherein a location on the substrate of each of the coupled split ring resonators in the array of coupled split ring resonators has an overlap with at least one other one of the coupled split ring resonators in the array of coupled slit ring resonators.

12. The method of claim 2 further comprising:
positioning each of the coupled split ring resonators in the array of coupled split ring resonators at a location on the substrate to have an overlap with at least one other one of the coupled split ring resonators in the array of coupled split ring resonators.

13. The method of claim 3, wherein the portion of the patient's anatomy is the patient's brain.

14. The method of claim 3, wherein the MRI image is obtained at a field strength of at least 7 T.

15. The method of claim 3, wherein the each of the coupled split ring resonators in the array of coupled split ring resonators inductively couple to a radiofrequency coil of the MRI device to provide additional flux during a transmit phase of the MRI device.

16. The method of claim 3, wherein the each of the coupled split ring resonators in the array of coupled split ring resonators inductively couple to a radiofrequency coil of the MRI device to improve receive MR signal during a receive phase of the MRI device.

17. The method of claim 3, wherein each of the coupled split ring resonators in the array of coupled split ring resonators generate a local magnetic field that increases resonator signal intensity near the coupled split ring resonator during operation of the MRI device.

18. The device of claim 7, wherein the substrate has a thickness of about 200 micrometers.

19. The device of claim 11, wherein the overlap is based on a critical loop center-to-center distance value to reduce inductive coupling.

* * * * *